US006827899B2

(12) United States Patent
Maisey et al.

(10) Patent No.: US 6,827,899 B2
(45) Date of Patent: Dec. 7, 2004

(54) TEST DEVICE

(75) Inventors: Graeme Antony Maisey, Chessington (GB); James Aitken, Dartford (GB); Andrew James Woodhead, London (GB); Stuart Richard May, Chessington (GB); Michael Pearson, West Molesey (GB); Murdo M. Black, Ipswich (GB); James George Elcoaté Smith, Abbeydale (GB)

(73) Assignee: Hypoguard Limited, Suffolk (GB)

( * ) Notice: Subject to any disclaimer, the term of this patent is extended or adjusted under 35 U.S.C. 154(b) by 62 days.

(21) Appl. No.: 09/943,647

(22) Filed: Aug. 30, 2001

(65) Prior Publication Data
US 2002/0057993 A1 May 16, 2002

Related U.S. Application Data
(60) Provisional application No. 60/232,166, filed on Sep. 11, 2000.

(30) Foreign Application Priority Data
Aug. 30, 2000 (GB) .............................................. 0021219

(51) Int. Cl.[7] .............................................. G01N 33/49
(52) U.S. Cl. ........................... 422/61; 422/63; 422/104; 436/44; 436/811; 436/808; 436/68; 436/95; 436/150; 221/167; 221/232; 221/268; 204/403.01; 204/403.02; 204/403.15; 204/407
(58) Field of Search .............................. 422/58, 61, 63, 422/64, 66, 100, 102, 104; 436/44–46, 808, 811, 63, 68, 95, 150; 204/403.1, 403.2, 403.15, 407; 221/1, 156, 167, 232, 268

(56) References Cited
U.S. PATENT DOCUMENTS

| 5,282,950 A | 2/1994 | Dietze et al. |
| 5,395,504 A | 3/1995 | Saurer et al. |
| 5,407,554 A | 4/1995 | Saurer |
| 5,525,297 A | 6/1996 | Dinger et al. |
| 5,660,791 A * | 8/1997 | Brenneman et al. .......... 92/132 |
| 5,797,693 A | 8/1998 | Jaeger |
| 5,810,199 A | 9/1998 | Charlton et al. |
| 5,872,713 A | 2/1999 | Douglas et al. |
| 6,534,017 B1 * | 3/2003 | Bottwein et al. .......... 422/104 |

FOREIGN PATENT DOCUMENTS

| DE | 2652370 | 5/1978 |
| DE | 29620368 U1 | 3/1997 |
| DE | 19639226 A1 | 3/1998 |
| DE | 19715031 A1 | 10/1998 |
| EP | 0373413 | 6/1990 |
| EP | 0455508 A1 | 11/1991 |
| EP | 0732590 A2 | 9/1996 |
| EP | 0738666 A2 | 10/1996 |
| EP | 0811843 A2 | 12/1997 |
| EP | 0877250 A2 | 11/1998 |
| EP | 0909952 A2 | 4/1999 |
| WO | WO92/17778 | 10/1992 |
| WO | WO 94/10558 | 5/1994 |
| WO | WO94/19685 | 9/1994 |
| WO | WO97/48979 | 12/1997 |
| WO | WO98/19159 | 5/1998 |
| WO | WO99/13100 | 3/1999 |

* cited by examiner

Primary Examiner—Lyle A. Alexander
(74) Attorney, Agent, or Firm—Thompson Coburn LLP

(57) ABSTRACT

A test device for testing of analyte concentration in a fluid comprises: a housing (2) having an opening and containing a stack of sensors (16); a transport member (4) rotatably mounted in the opening of the housing, having an axis of rotation which spans the opening; a spring (24) which urges the stack against the transport member; and sealing means (20, 34) for making a moisture tight seal between the transport member and the sensors when the transport member is in a specified rotational position. An outer surface of the transport member has a recessed region (12) which is adapted to receive a single sensor from the stack. Rotation of the transport member with a sensor in the recessed region transports the sensor to a location where it can be connected to a meter (6, 8) and receive a drop of fluid to be tested.

27 Claims, 42 Drawing Sheets

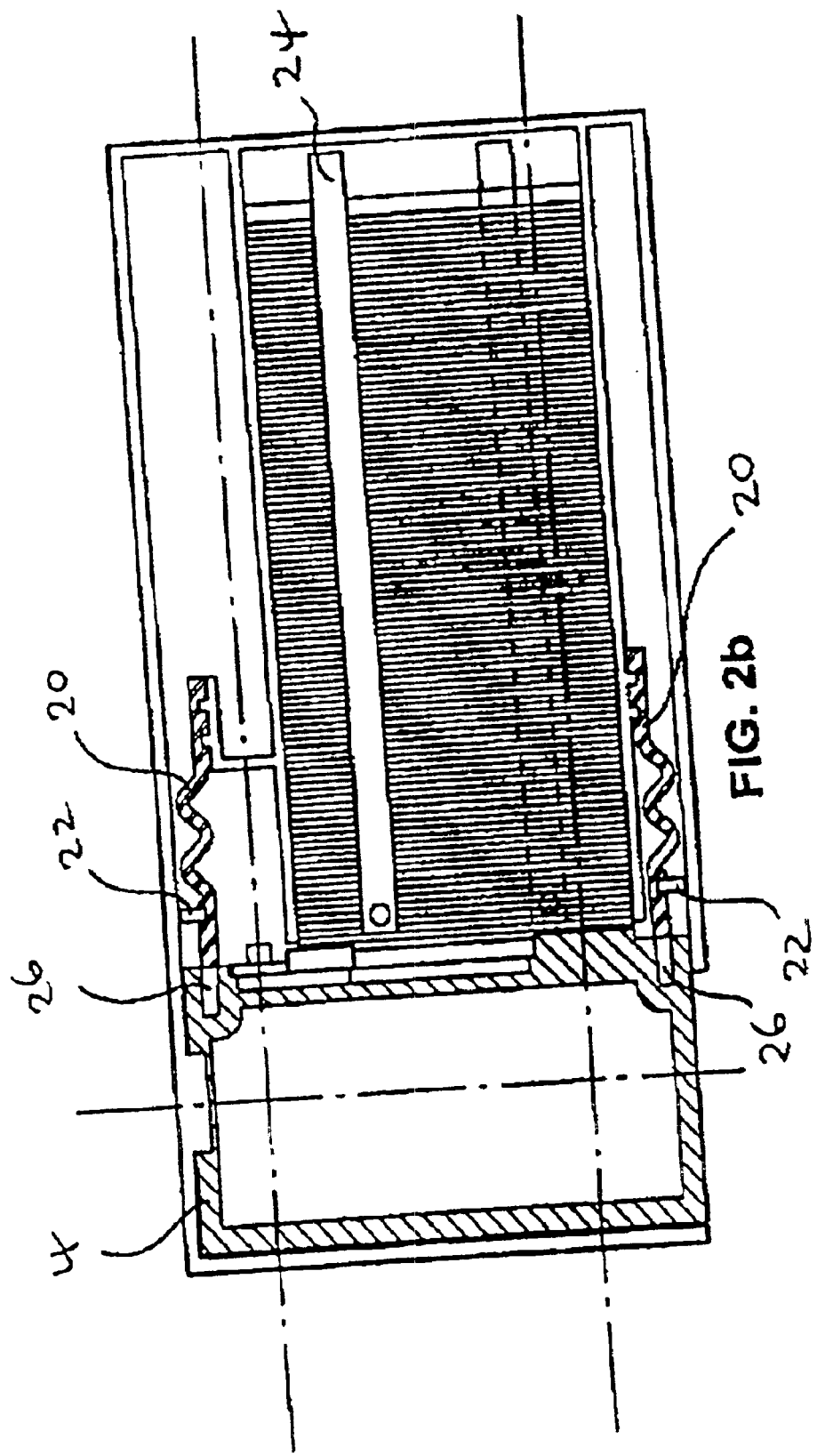

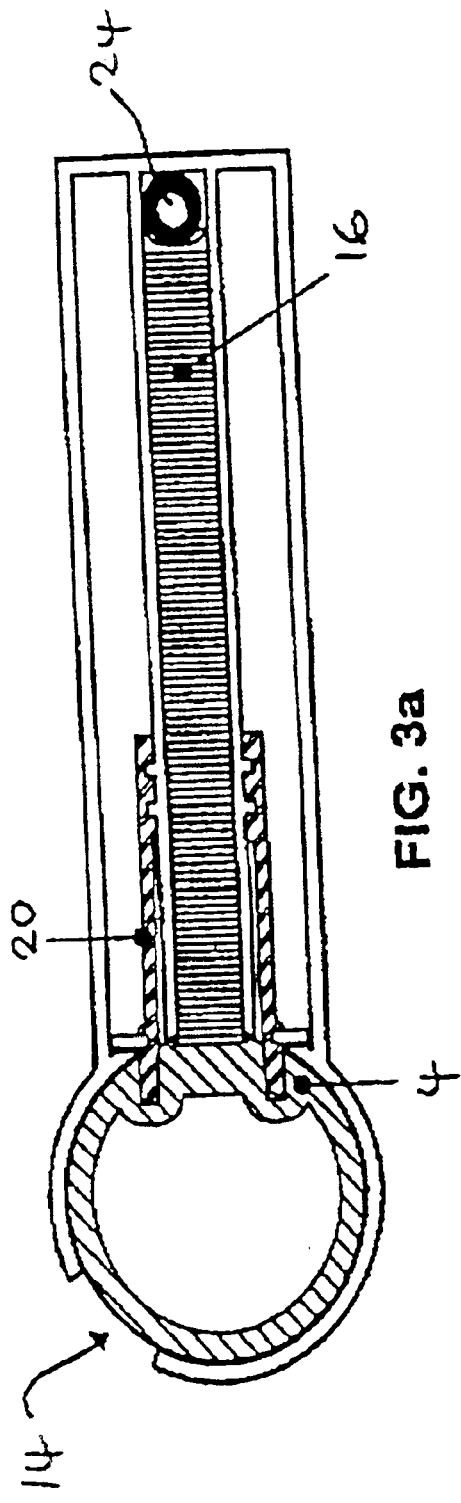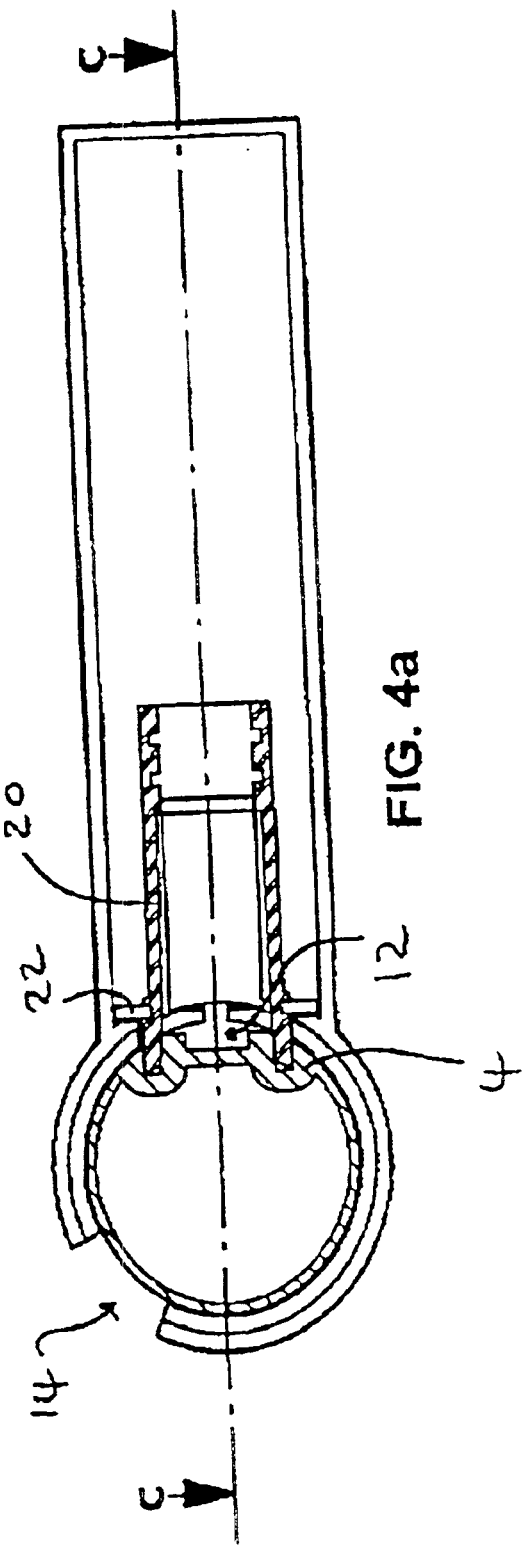

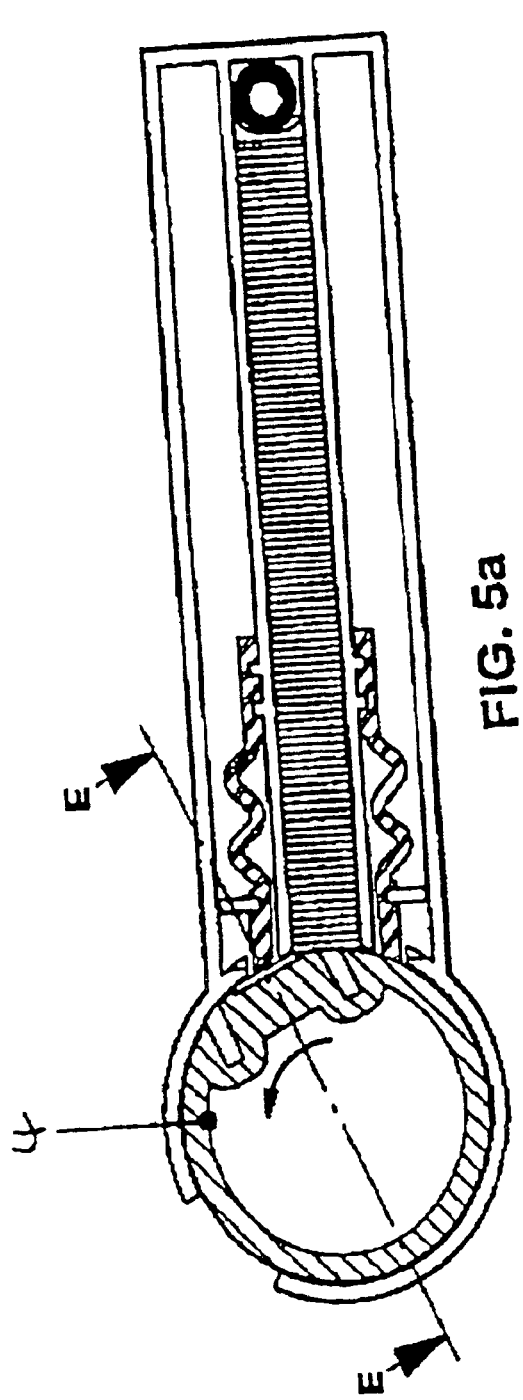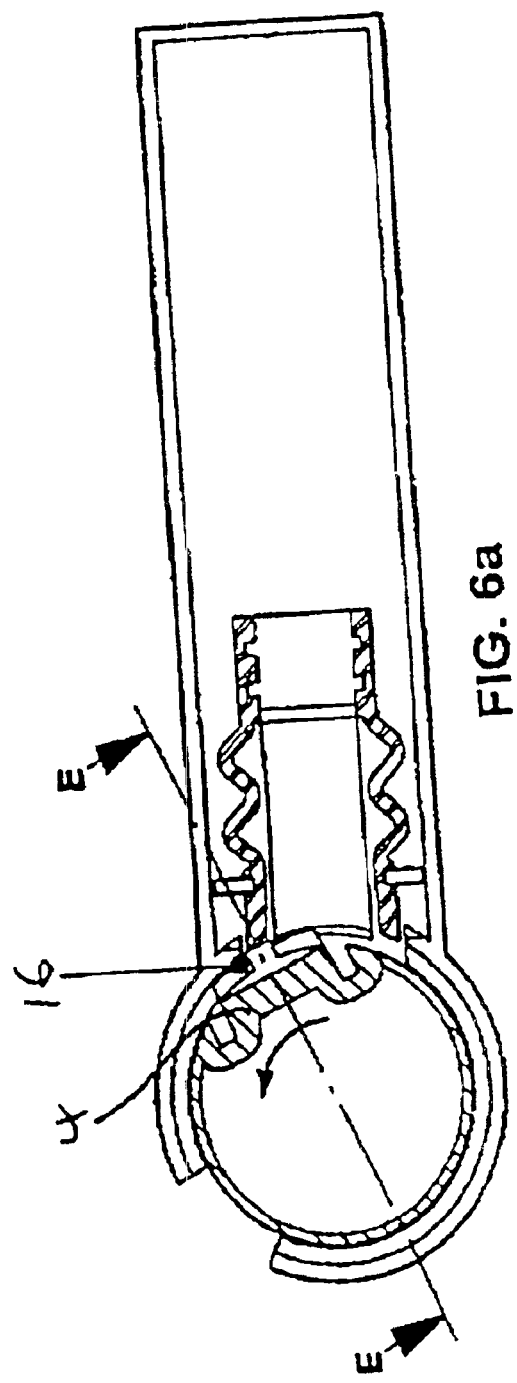

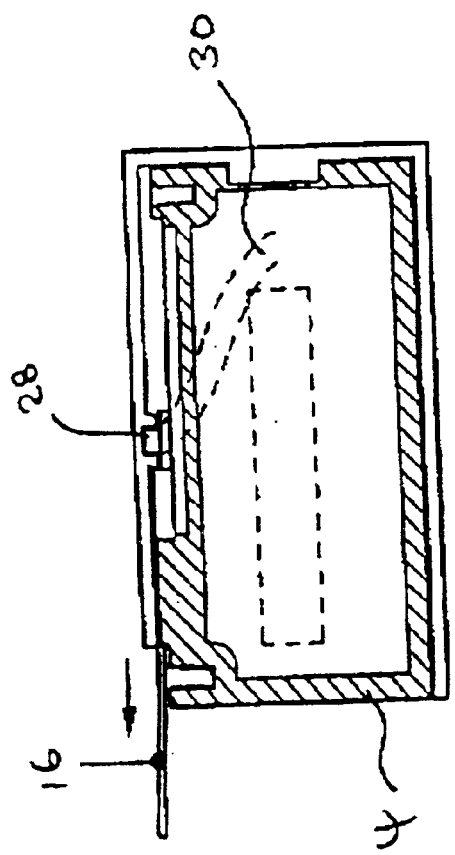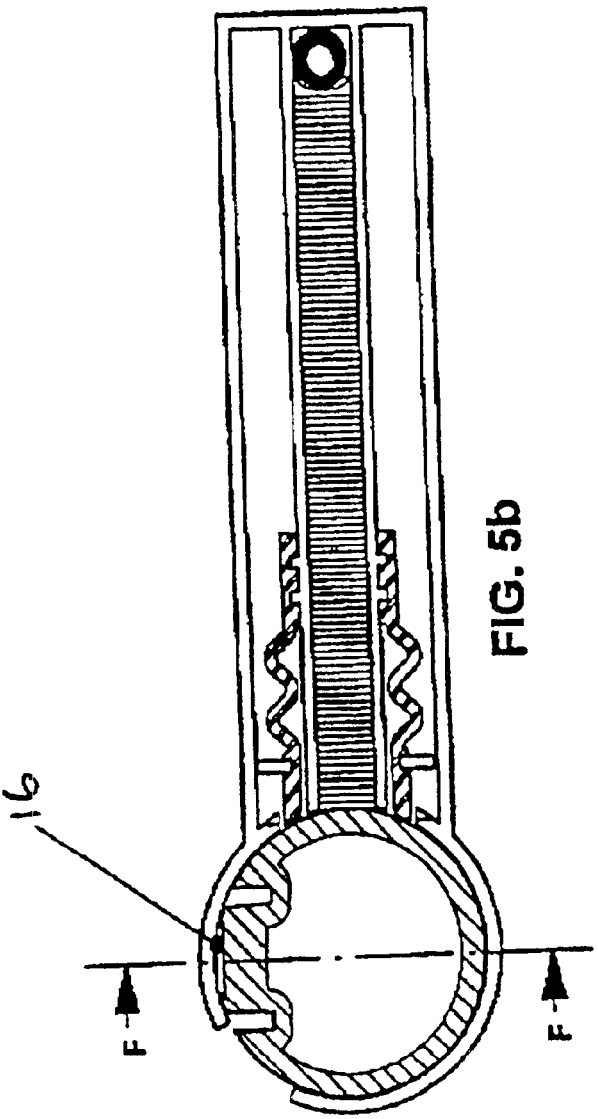

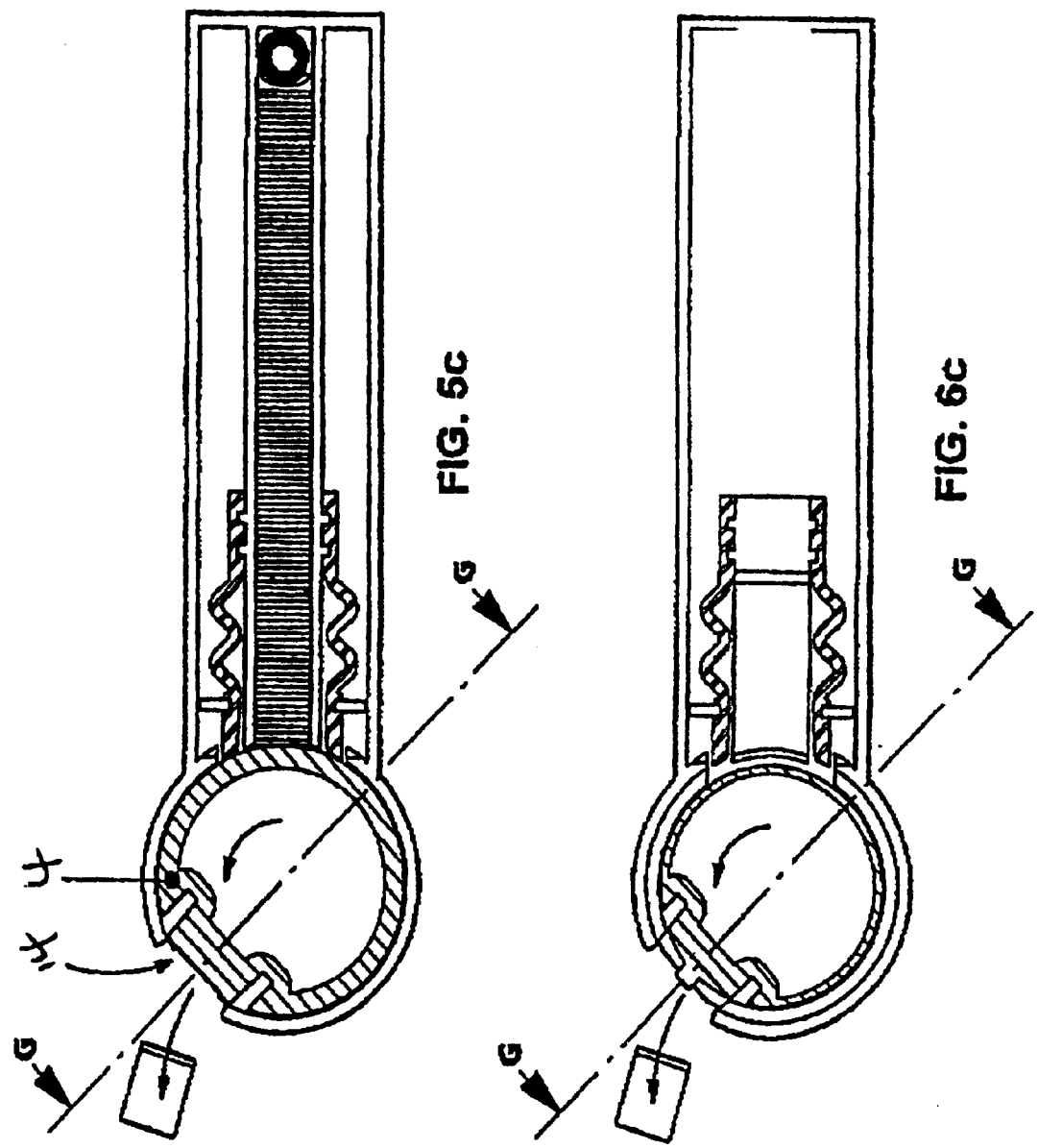

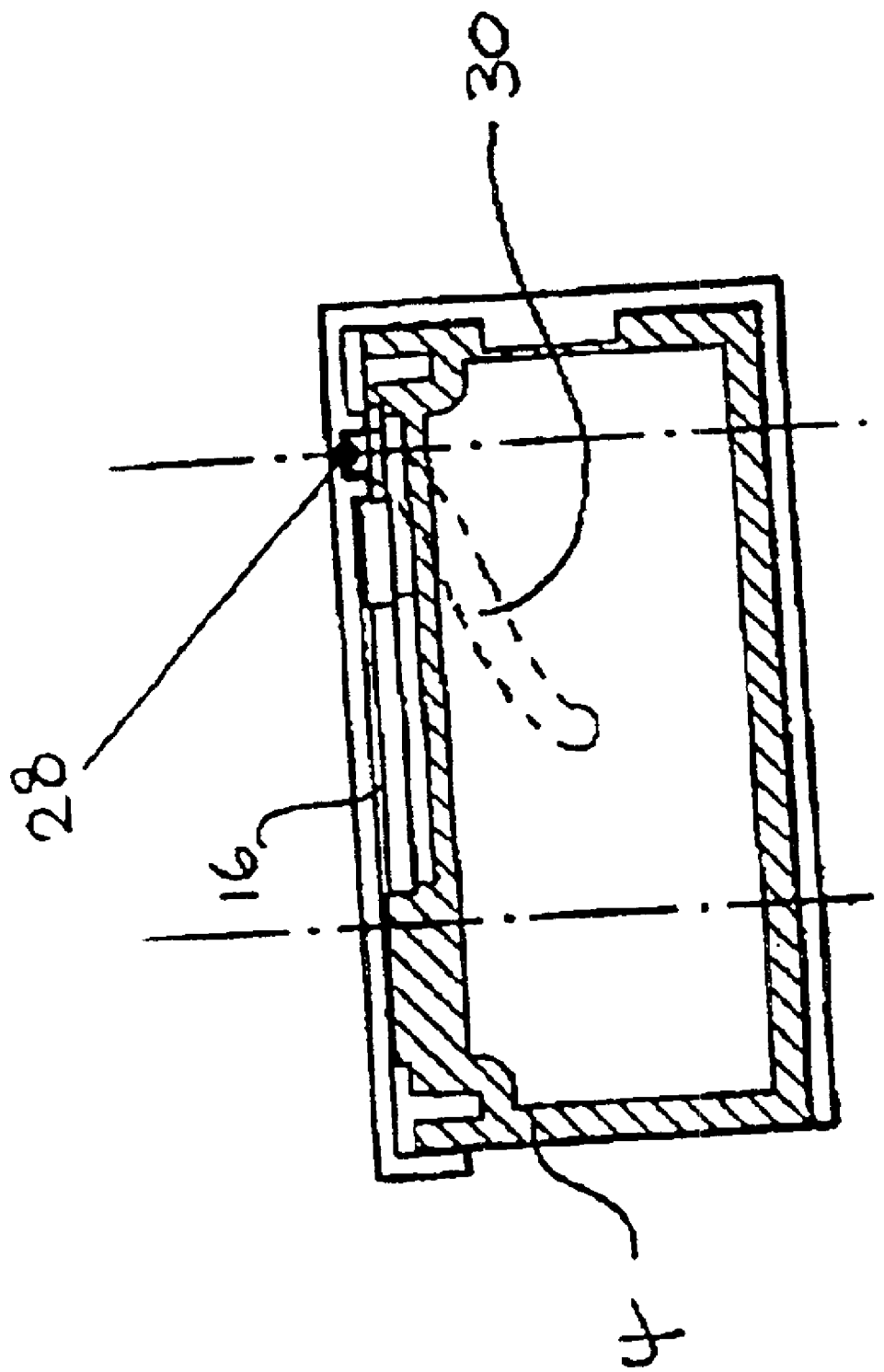

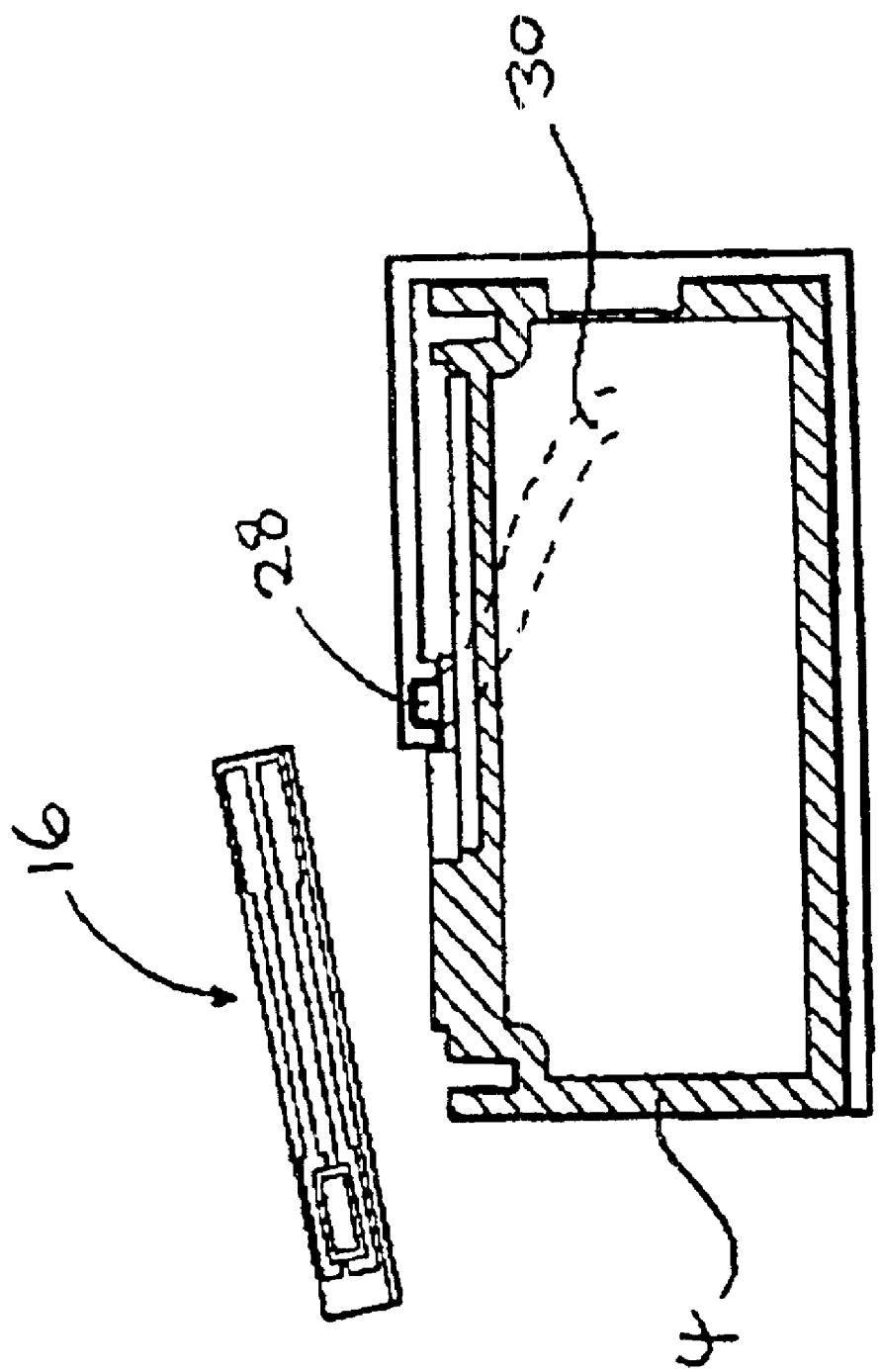

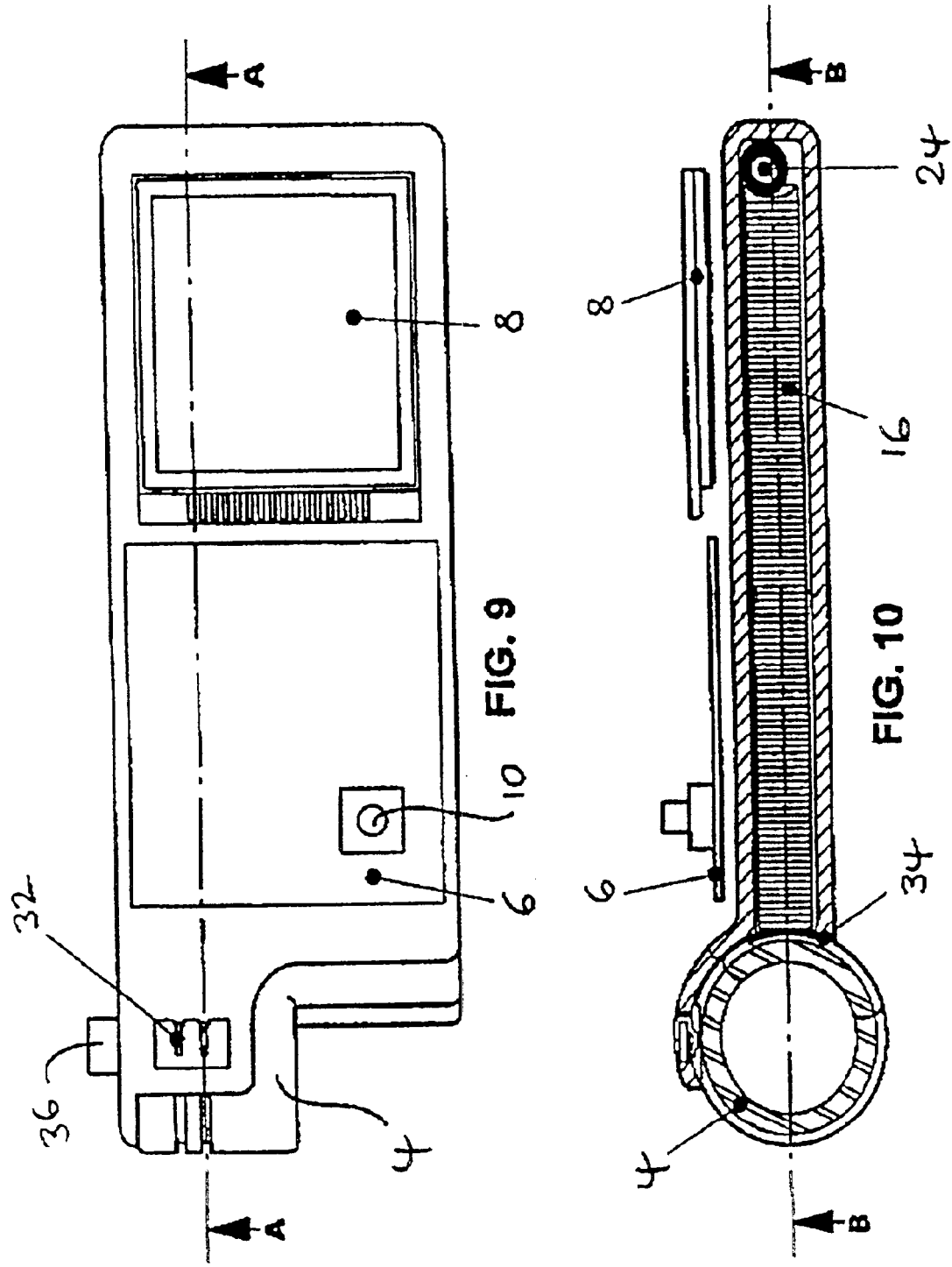

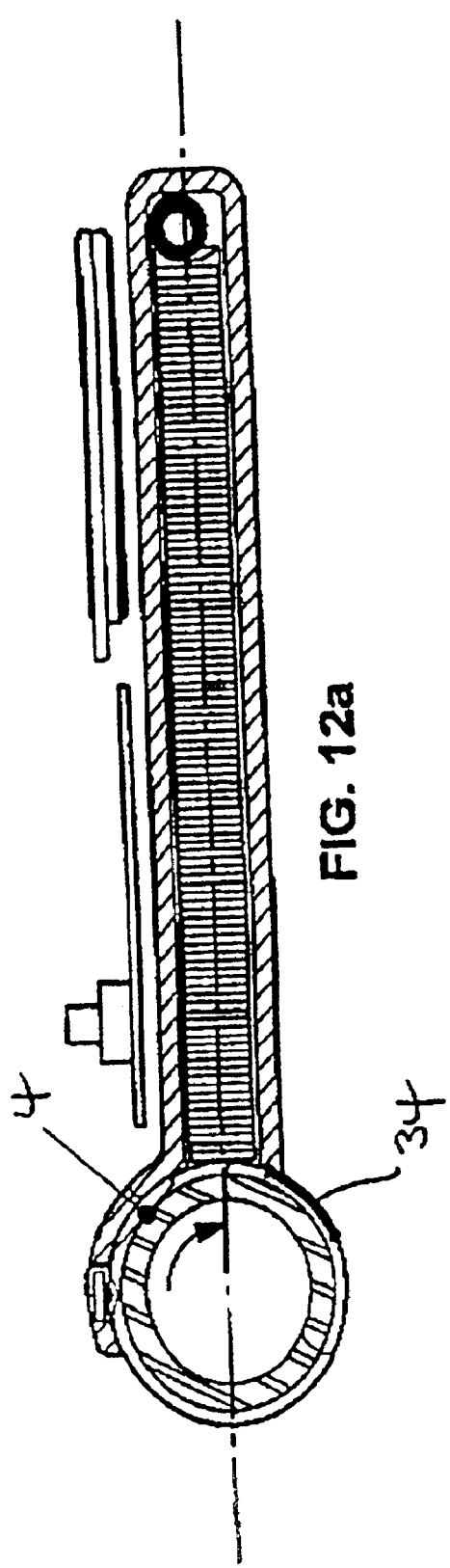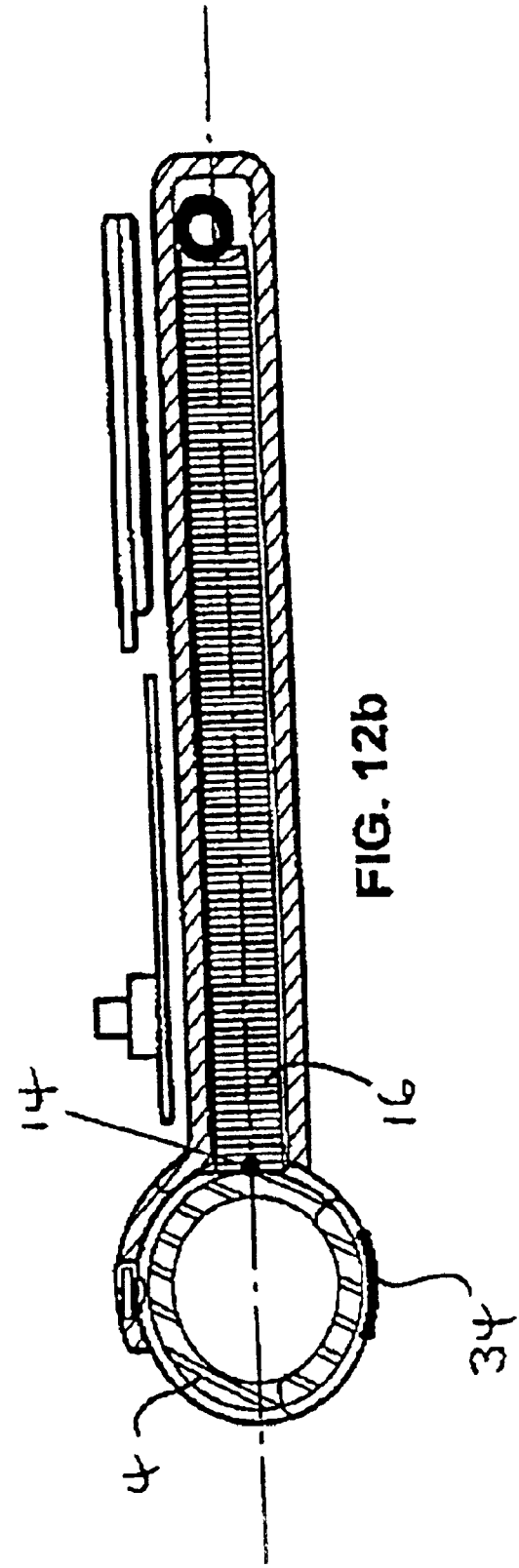

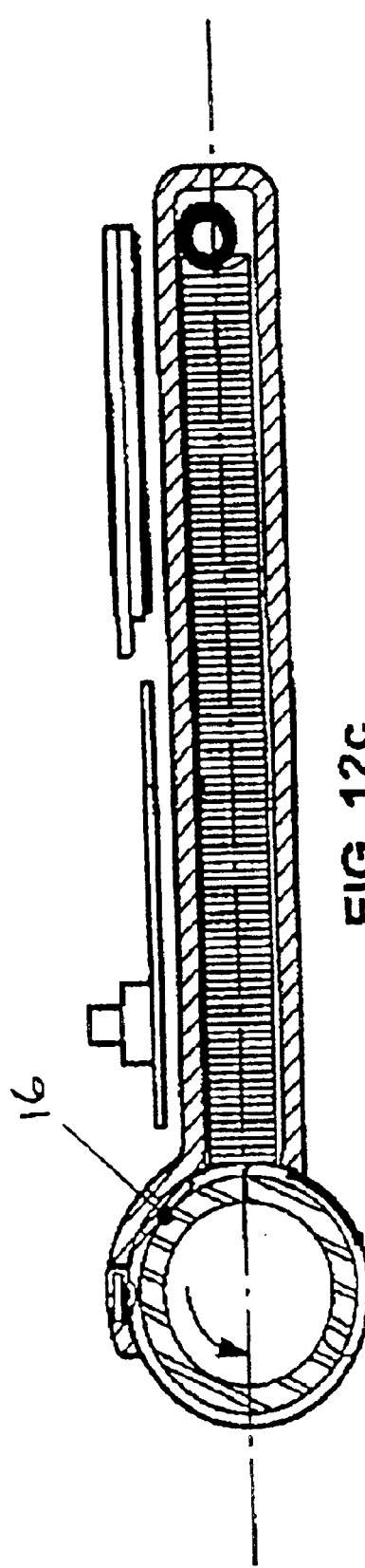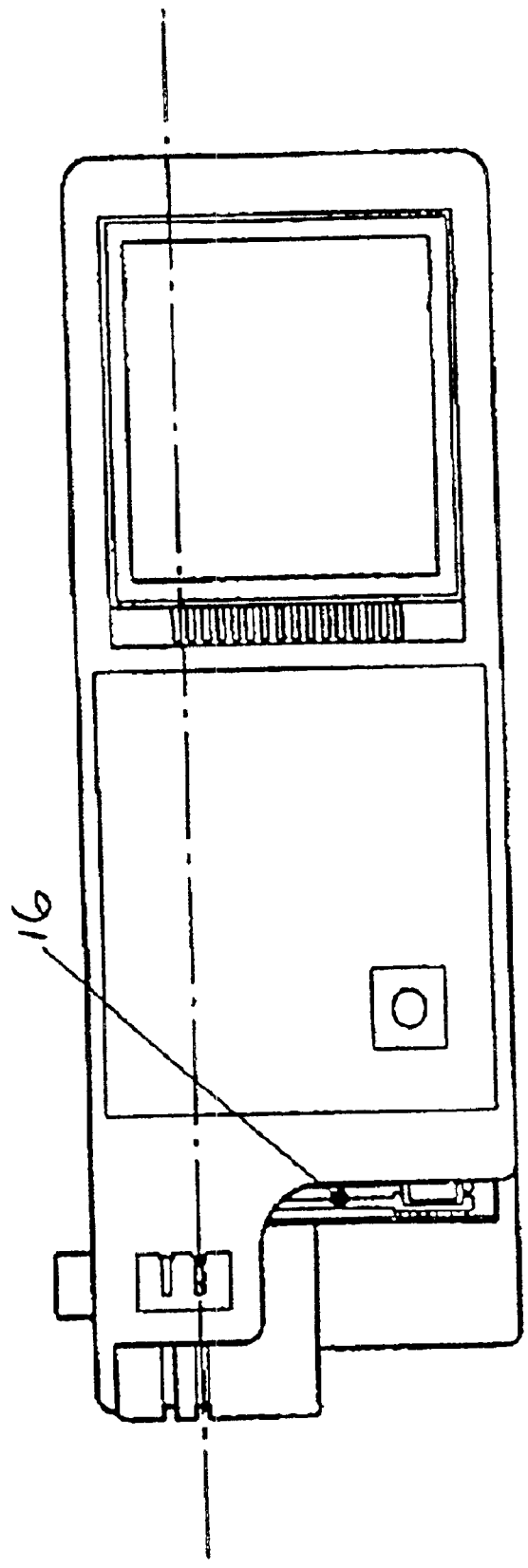
FIG. 12c
FIG. 13a

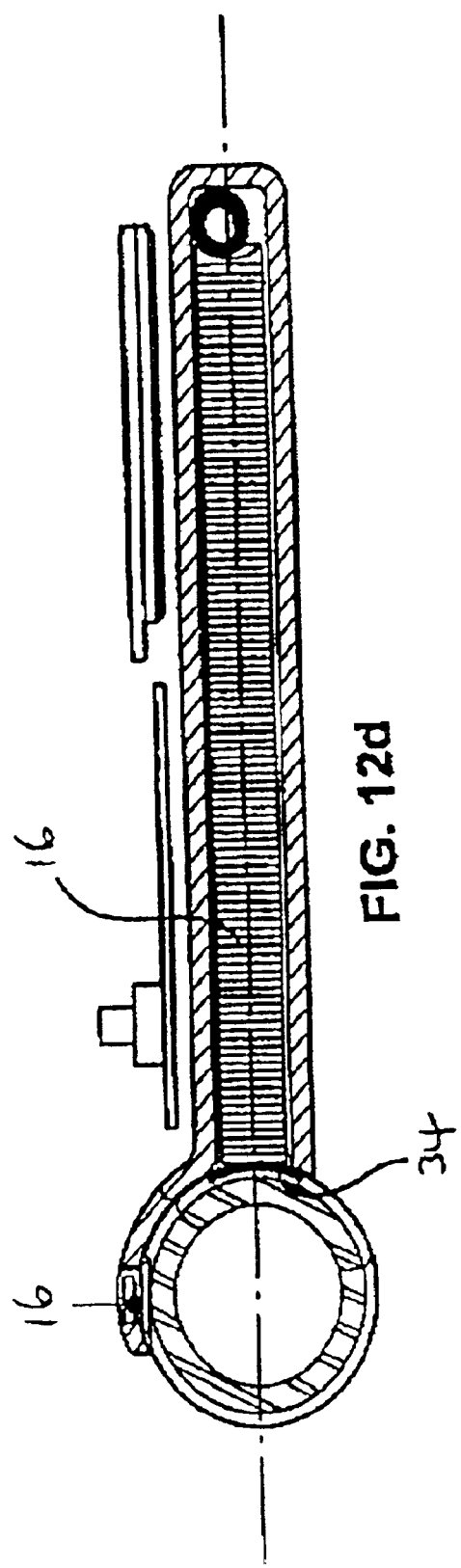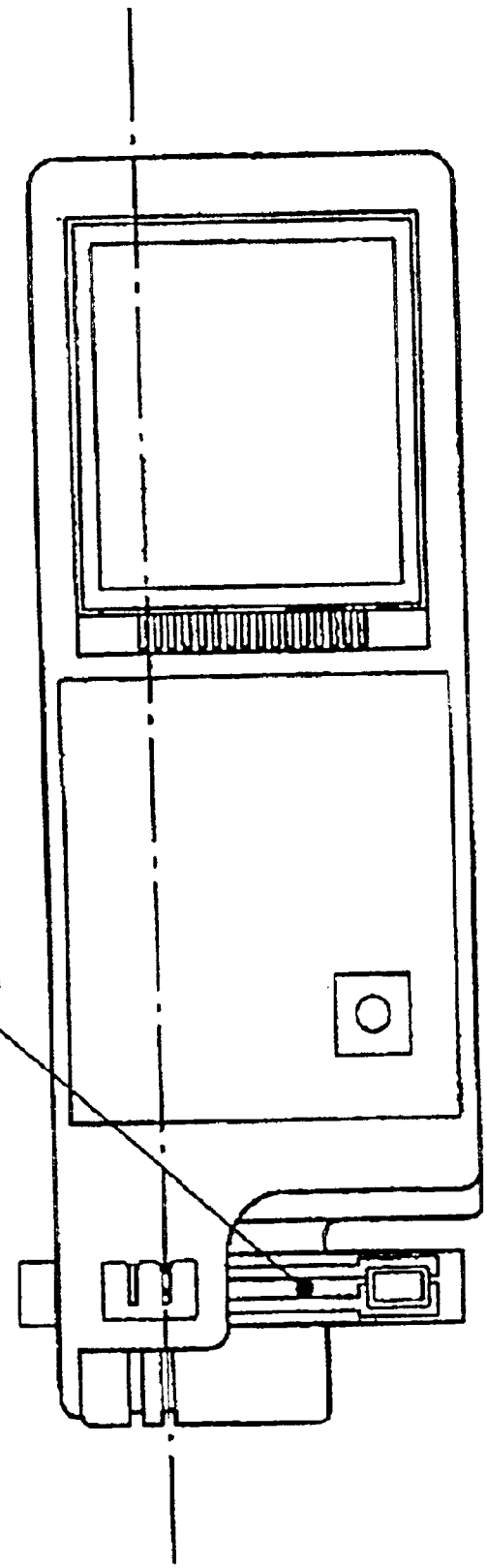

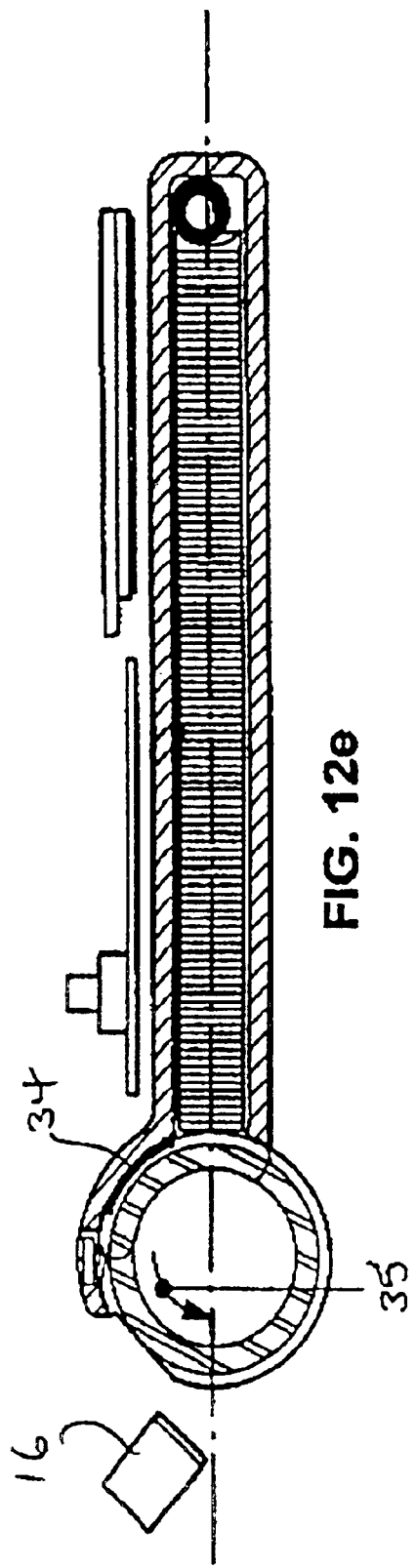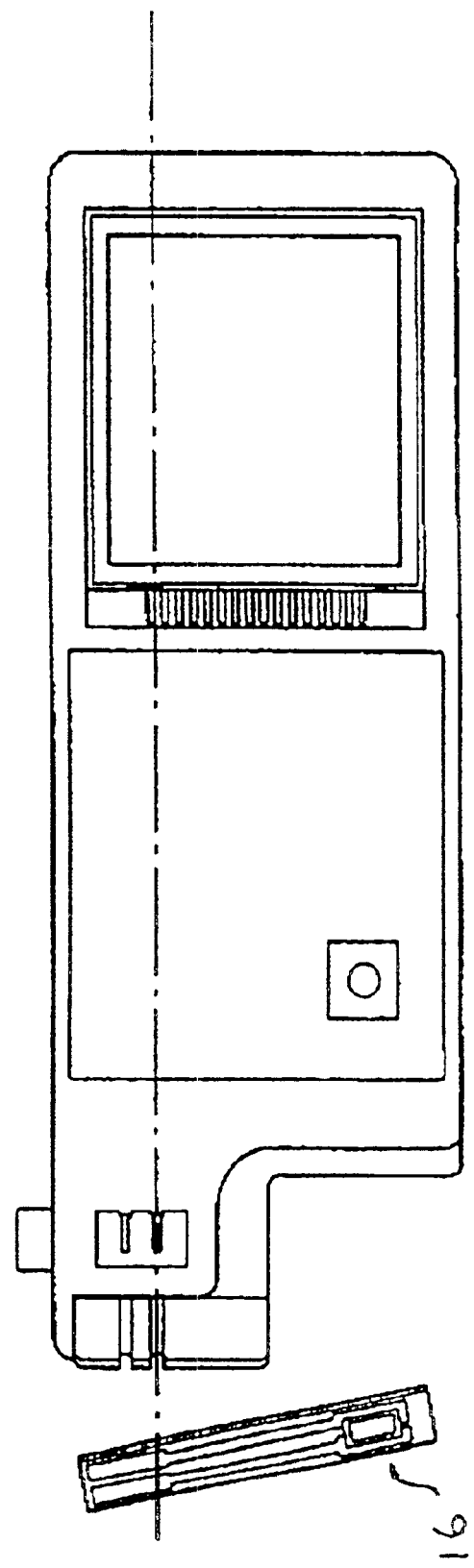

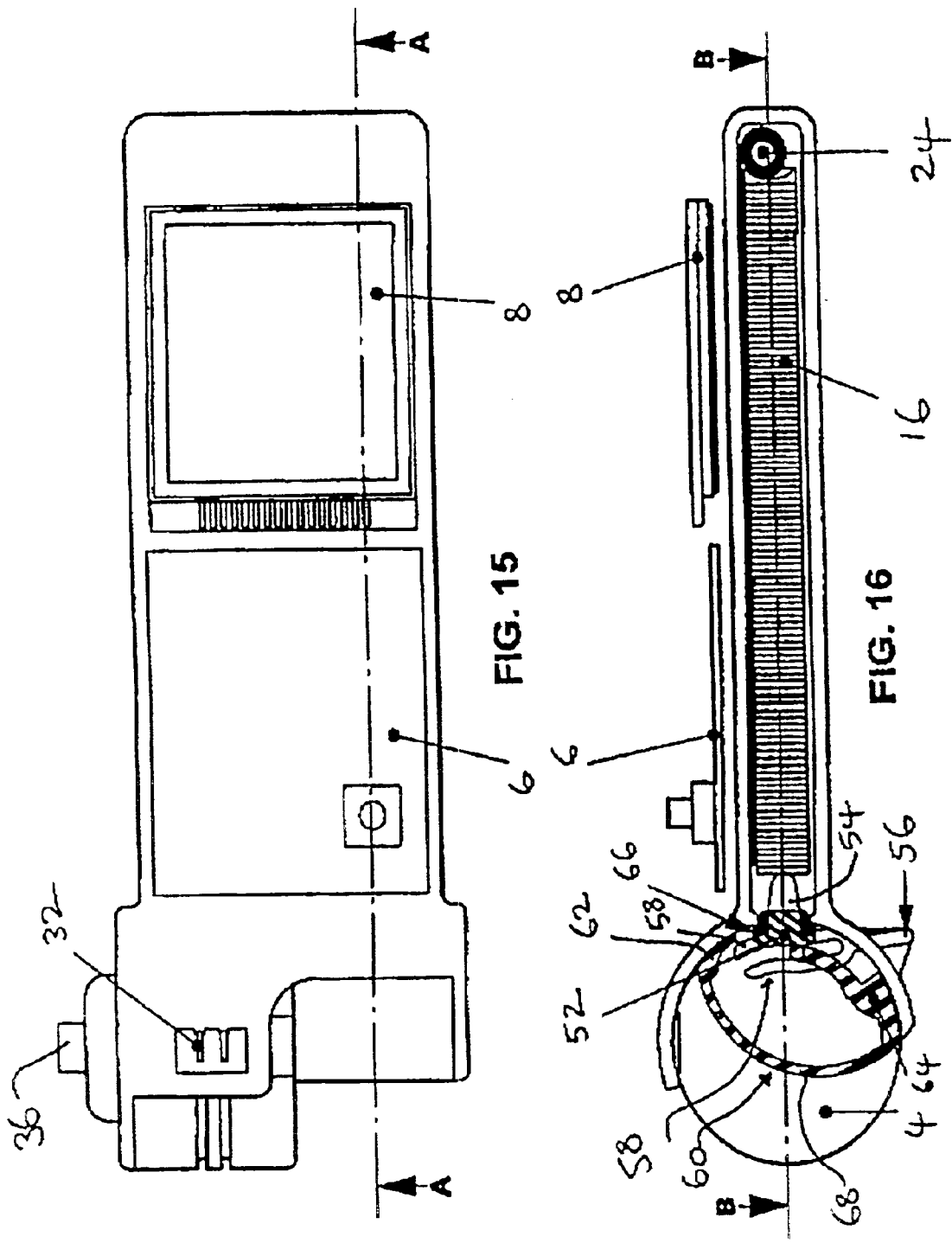

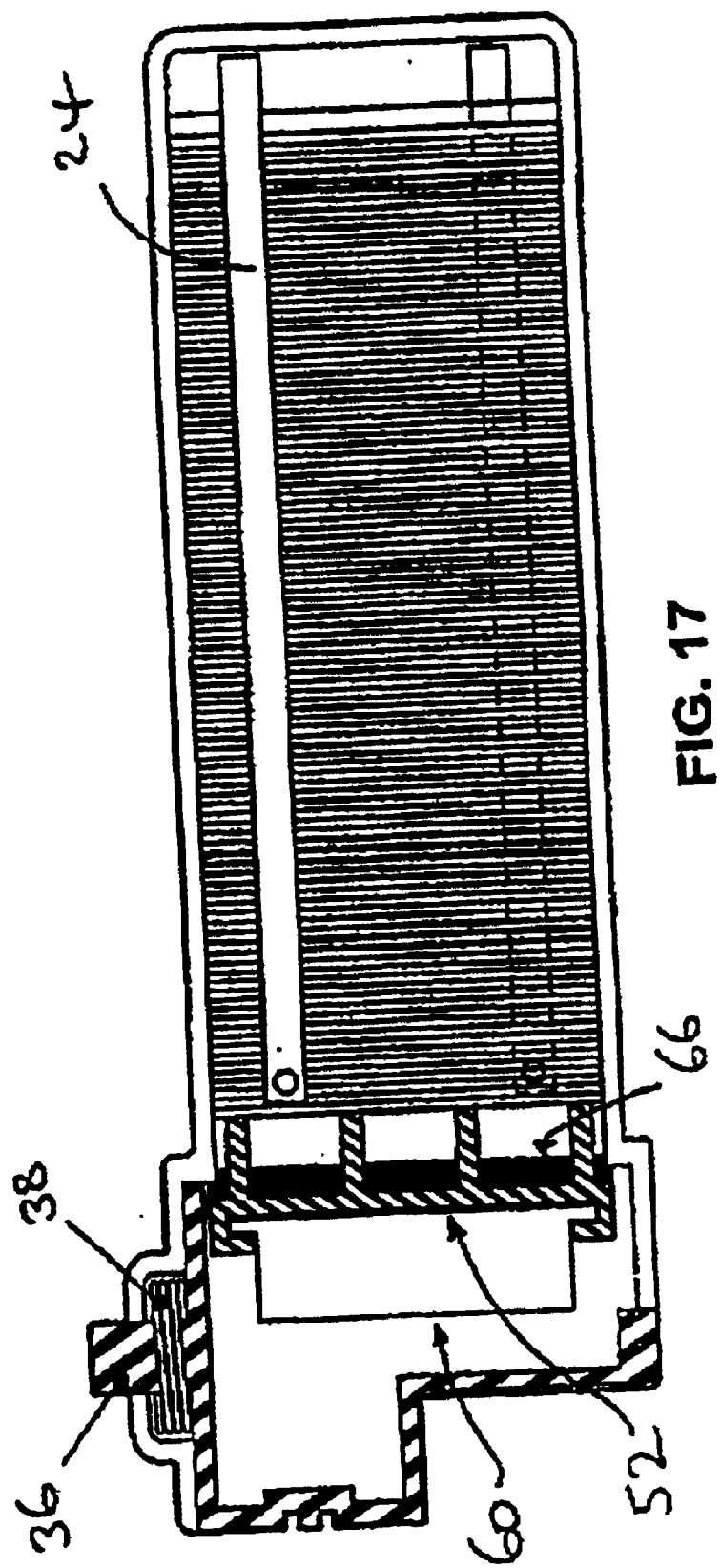

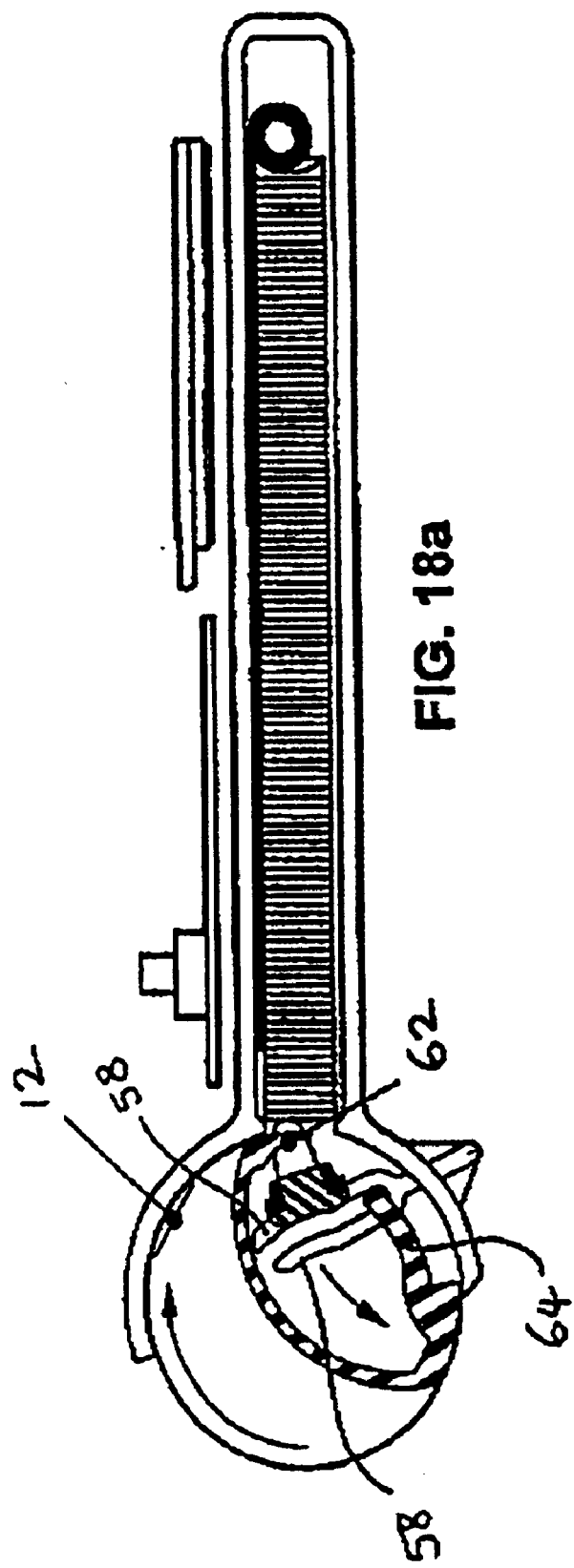
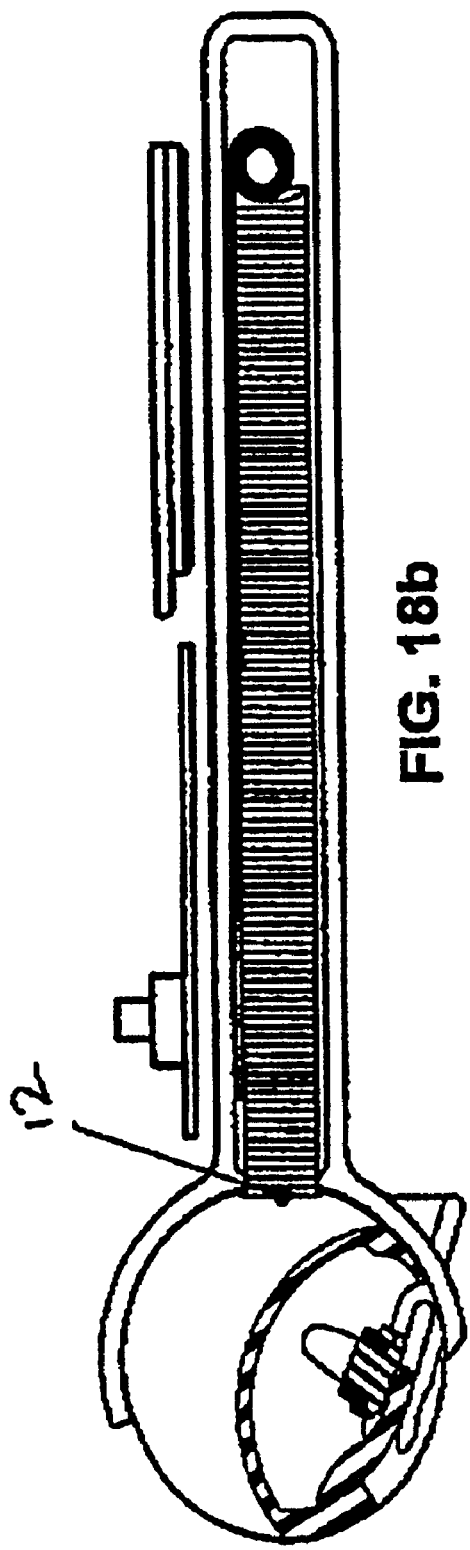

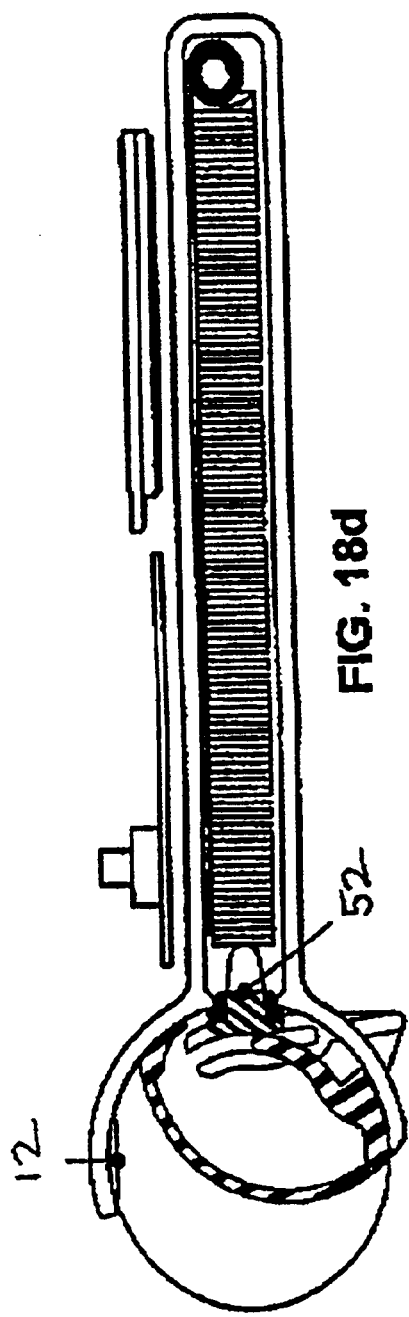
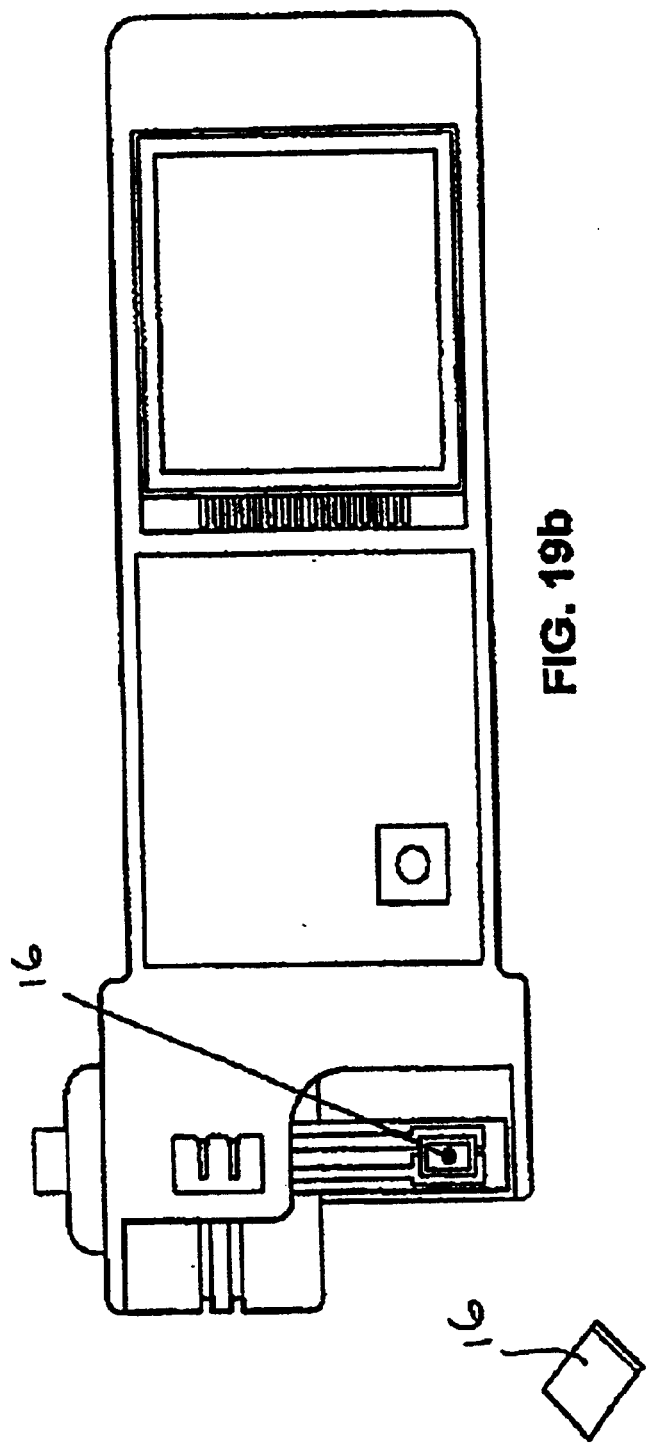

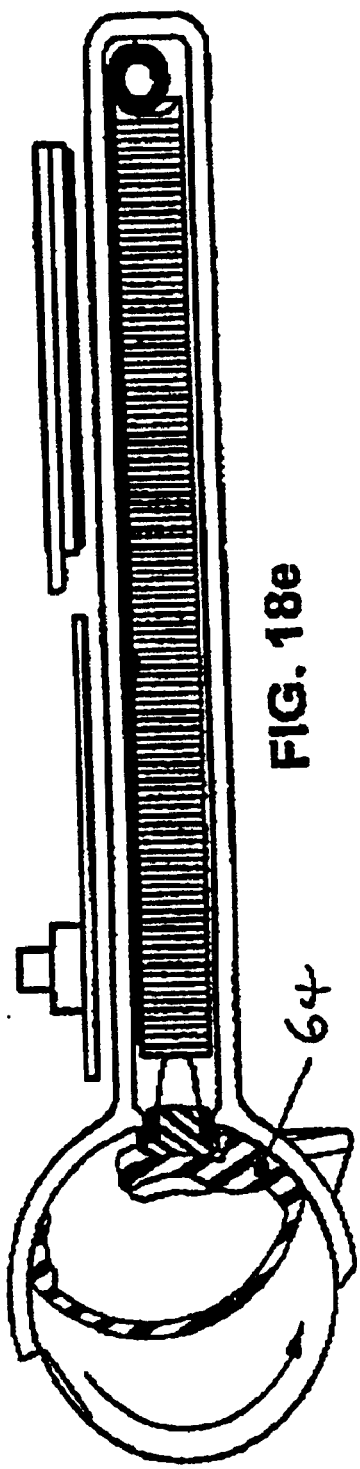
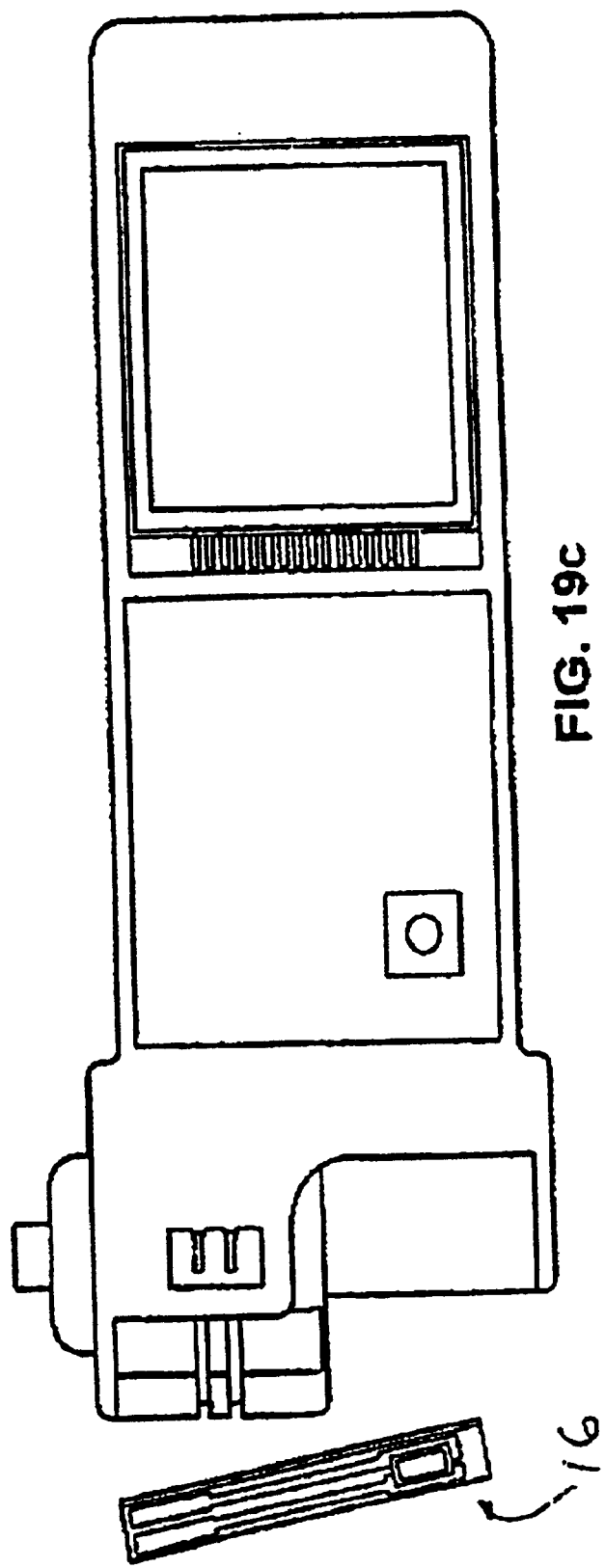
FIG. 18e
FIG. 19c

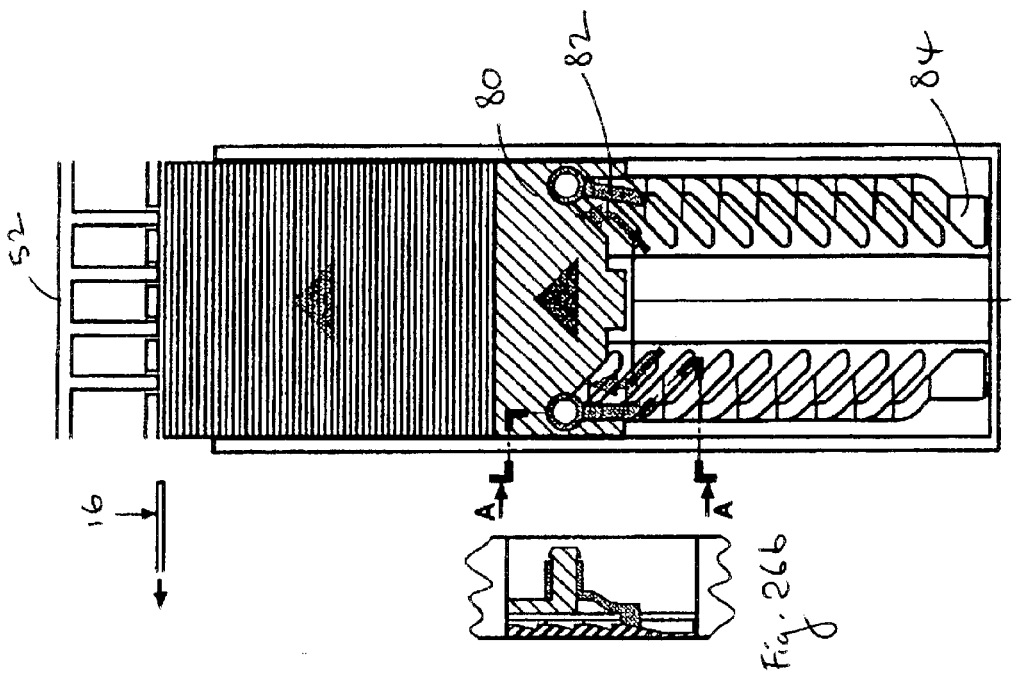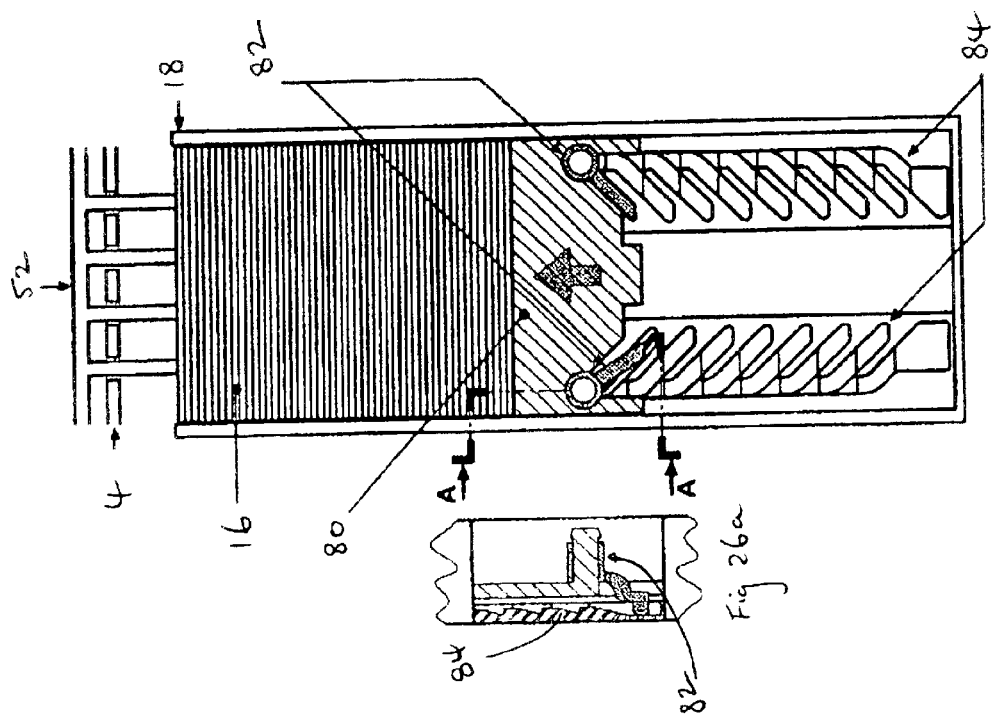

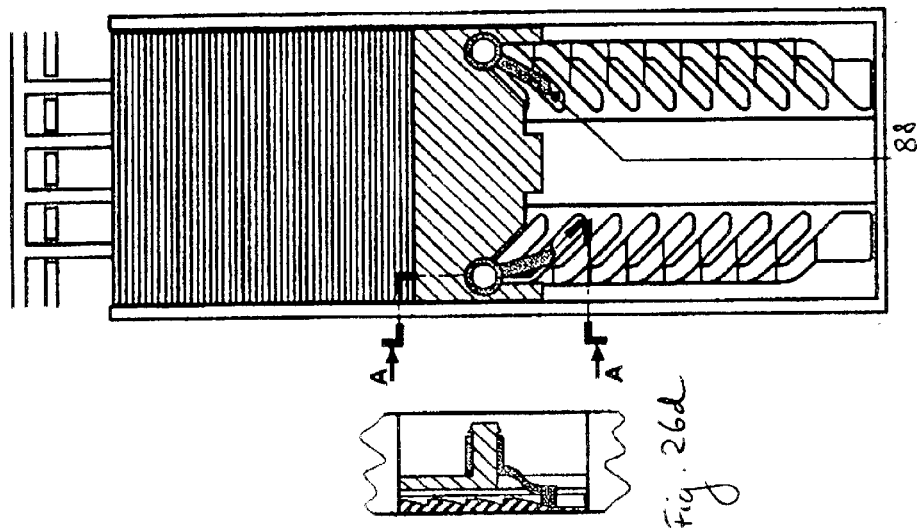
Fig. 25d
Fig. 26d
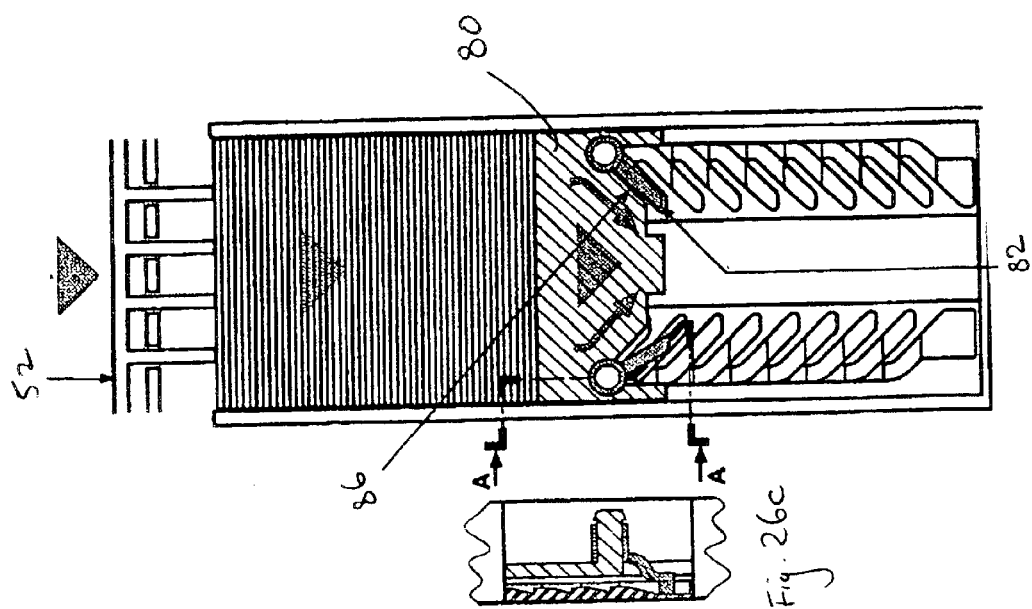
Fig. 25c
Fig. 26c

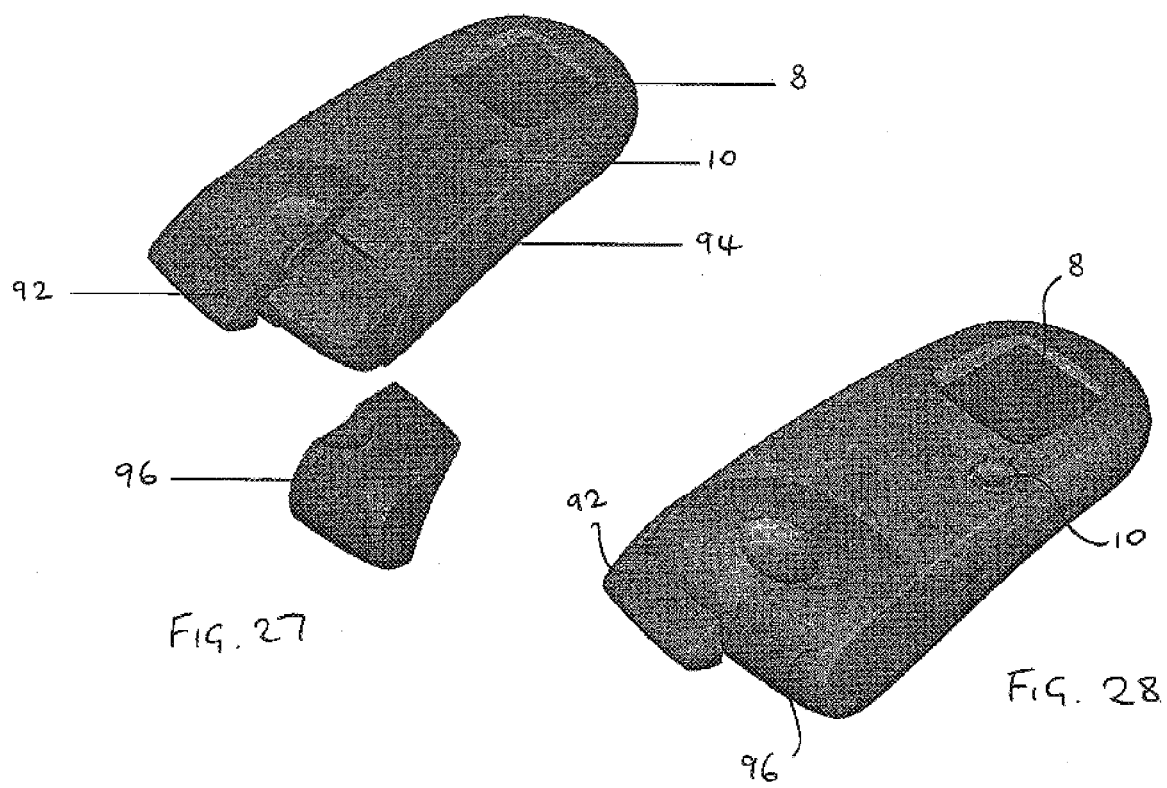

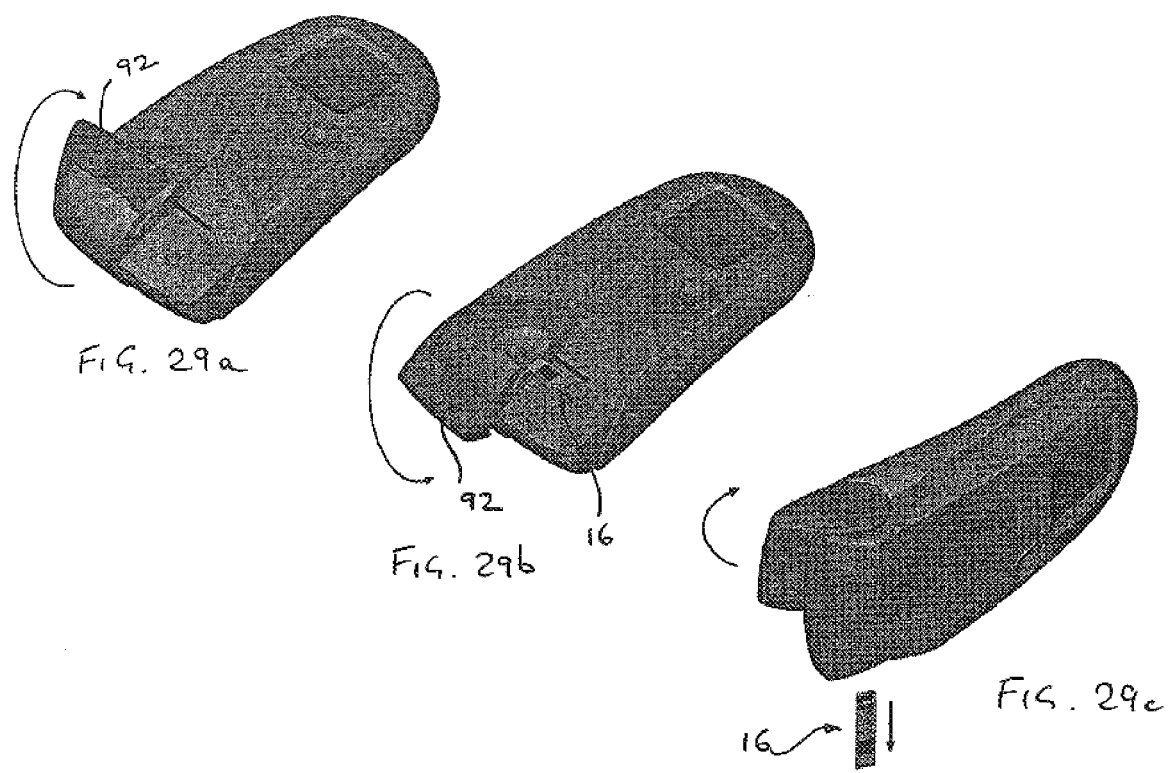

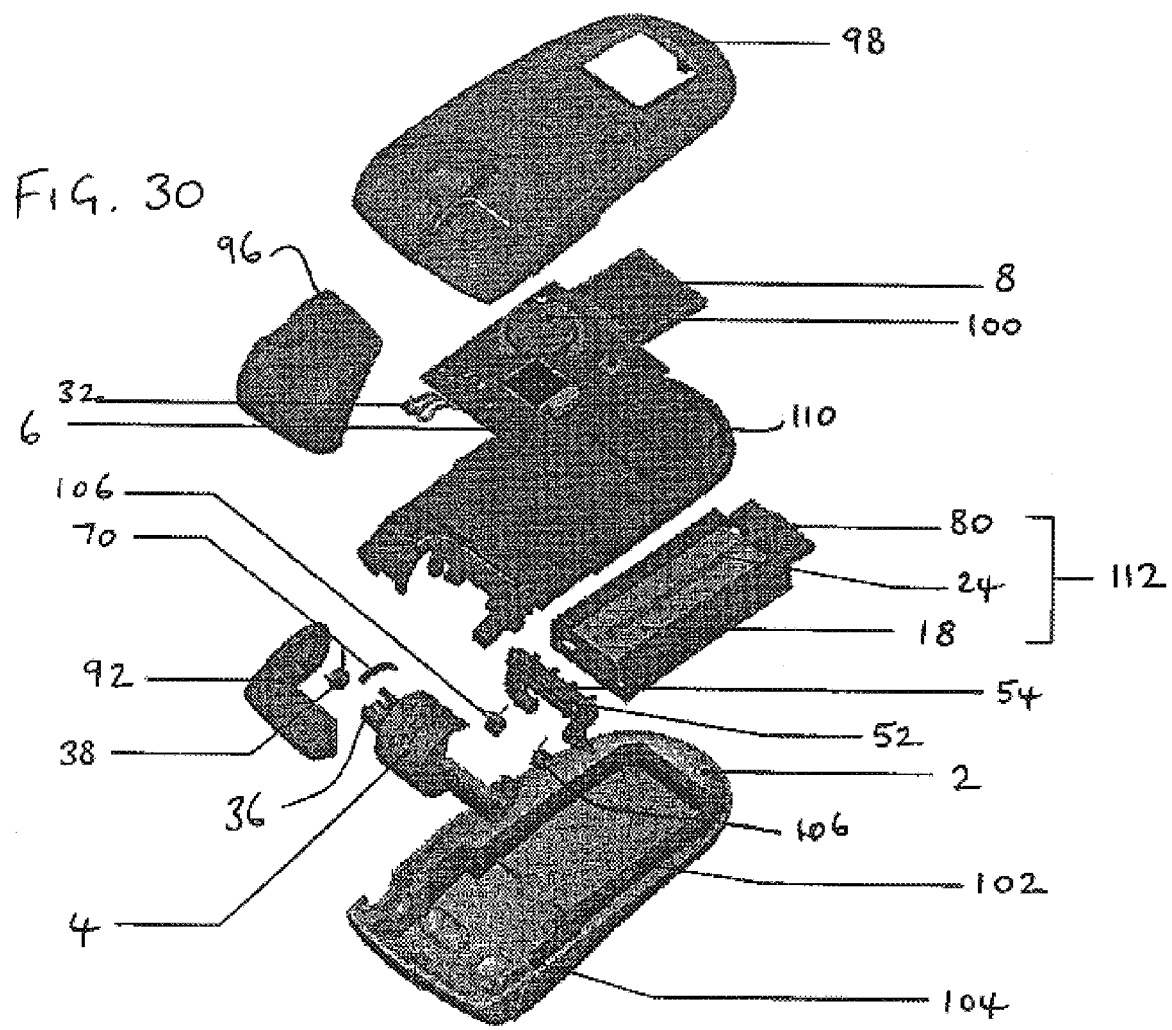

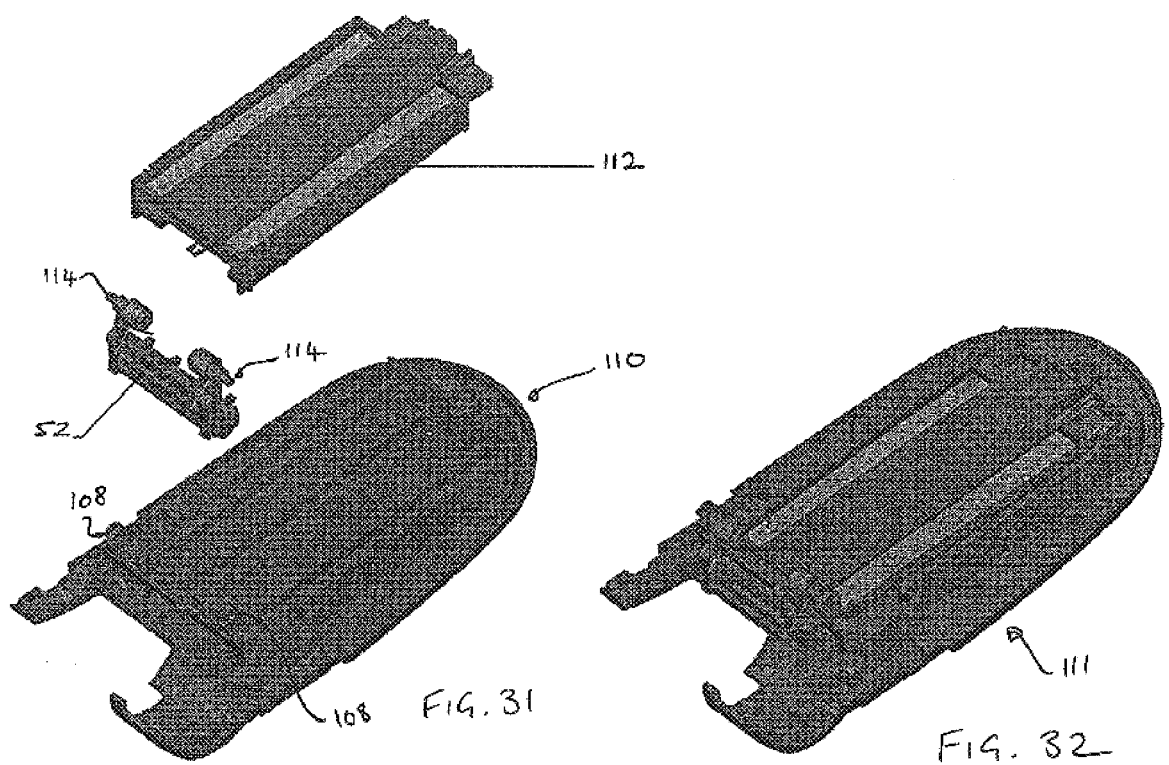

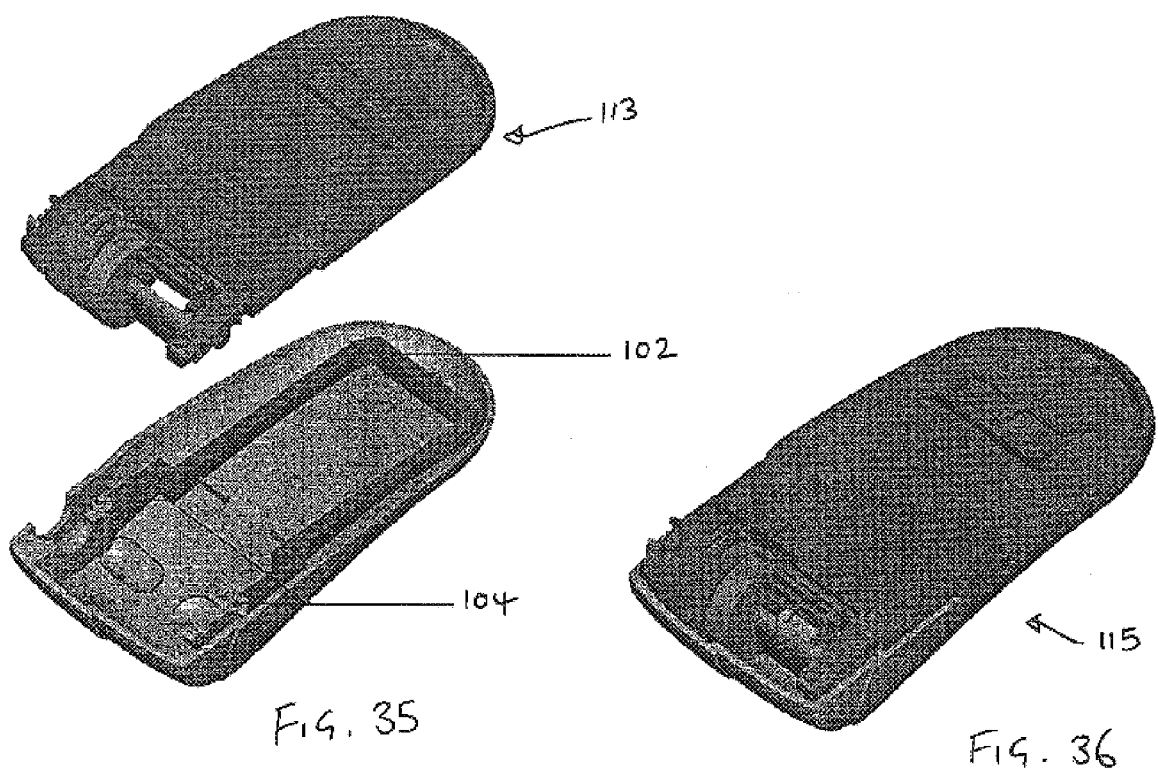

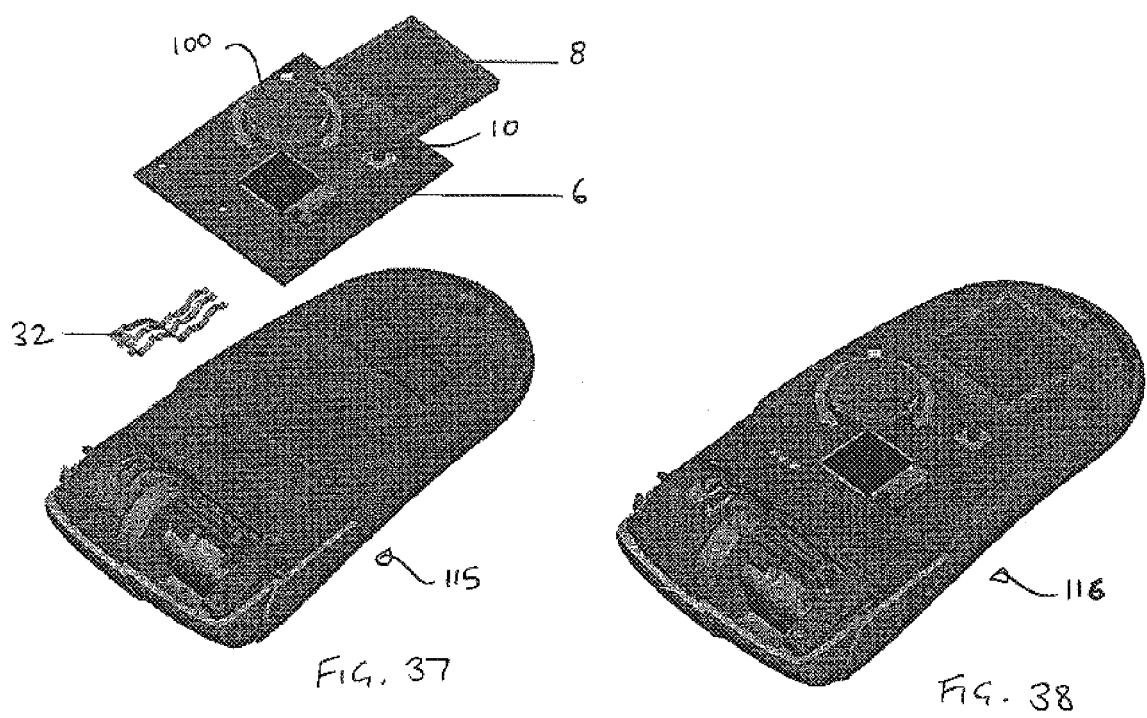

TEST DEVICE

This application claims benefit of U.S. Provisional application Ser. No. 60/232,166, filed Sep. 11, 2000.

BACKGROUND OF THE INVENTION

1. Field of the Invention

The present invention relates to a test device for measuring the concentration of an analyte in a fluid sample, notably to a test device for analysing blood glucose or other analytes in bodily fluids.

2. Description of the Prior Art

Diabetics regularly need to test samples of their blood to determine the level of blood glucose. The results of such tests may be used to determine levels of medication needed to treat the diabetes at the time. In one known type of system, disposable sensors are used to test the blood. The sensors typically take the form of test strips which are provided with a reagent material that will react with blood glucose to produce an electrical signal. Conductive tracks on the test strip relay the electrical signal to a meter which displays the result. After a sample of blood has been applied to the test strip and the measurement has been taken, the test strip is disposed of. In order to couple the conductive tracks on a test strip with the meter, the test strip needs to be inserted into a sensor holder prior to the start of testing. The sensor holder has corresponding electrodes which are brought into electrical contact with the conductive tracks of the test strip. Test devices are known in which a plurality of test strip are provided on a cartridge disc. Each strip is housed in its own sensor slot, and means are provided to eject a test strip from its slot when required, and to automatically locate it in a sensor holder. Examples of test devices with test strip dispensers are described in U.S. Pat. No. 5,660,791, European Patent Application No. 0 732 590, and European Patent Application No. 0 738 666.

A problem with test strips is that they have only a limited shelf life, and exposure of test strips to the atmosphere reduces the shelf life further. Test strips open to the atmosphere will typically have a shelf life of about two to three months, whereas test strips which are sealed from the atmosphere will have a shelf life of about six to 12 months.

It has been proposed in WO 94/10558 to provide a stack of disposable test elements in a cylindrical housing, the stack being urged towards a test station to form a liquid-proof seal. In DE 196 39 226 A1 it is proposed to provide a test device with a cartridge that may have a plurality of chambers containing test strips, each of which chambers may be individually sealed to preserve the shelf life of the strips therein. A user removes the seal for each chamber when required, and a timing circuit may be activated either by the user or when the cartridge is pushed into the device. After a set time period has elapsed, an alarm or other indication reminds the user that the time period for using the strips has elapsed.

It is an object of the present invention to provide an improved test device.

SUMMARY OF THE INVENTION

According to an aspect of the present invention there is provided a test device for testing of analyte concentration in a fluid to be applied thereto, the device comprising:

a) a plurality of sensors arranged in a stack, each of said sensors carrying reagent means for producing an electrical signal in response to the concentration of analyte in an applied fluid, each of said sensors having a plurality of electrode tracks for transmitting said electrical signal;

b) a housing having an opening therein and containing the said stack of sensors;

c) electrical contacts mounted in relation to the housing for engaging with electrode tracks on a sensor at an engagement location;

c) a meter connected to the said electrical contacts, having electronics means for producing a signal output which is dependent on the electrical signal from a sensor when the sensor is engaged with the said contacts;

d) a transport member rotatably mounted in the opening of the housing, having an axis of rotation which spans the opening and having an outer surface which is provided with a recessed region adapted to receive a single sensor from the stack;

e) spring means within the housing which urge the stack of sensors towards the transport member and which urge a single sensor into the said recess when the recess is suitably aligned adjacent to the stack;

f) sealing means for making a moisture tight seal between the transport member and the stack when the transport member is in a specified rotational position; and g) wherein rotation of the transport member with a sensor in the recessed region will transport the sensor to the engagement location or to a position where the sensor can be moved to the engagement location, whereby electrode tracks of the sensor can engage with the said electrical contacts.

With the transport member in a start or home position, the sealing means keeps moisture from sensors in the stack when the device is not being used. The device may be factory assembled under controlled temperature and humidity conditions, and kept sealed until a user is ready to use a sensor. In a preferred embodiment the sealing means also provide a moisture-proof seal when the sensor is in the engagement location, so that sensors in the stack are protected while an analyte measurement is being taken.

The invention will be described with reference to the testing of glucose concentrations in blood, but it will be understood that the invention is not limited to this embodiment and is of general applicability for testing analytes in bodily and other fluids.

The transport member may take the sensor to the engagement location by rotational motion alone. Additional pushing means may be provided to translate the test strip to the engagement location. Such pushing means may be provided by a captured pusher which engages with a track on the housing so as to move the test strip during rotation of the transport member. Alternatively, separately actuatable pushing means could be provided to push the sensor to the engagement location after rotation of the transport member to a suitable position. It will also be understood that other means could be provided for moving the test strip after it has been carried by the transport member, for example rotation or a combination of rotation and translation.

The electrical contacts may be brought automatically into contact with electrode tracks on the sensor in the engagement location, for example by means of spring biasing. Alternatively, the user could move the electrical contacts to achieve the necessary contact at the engagement location.

After a measurement has been taken, it would be possible to remove the used sensor from the engagement location by manual intervention from the user. However, to avoid the need for handling of the used sensor it is preferred that the transport member can be further rotated from the engagement location to an exit location at which the sensor can fall out or be pushed out by ejection means.

After completion of a test measurement, and ejection of the used sensor, the transport member is returned or advanced to the start position. This may be done manually by the user or by means of a motor. The transport member is preferably urged by a return spring to return to the start position.

For simplicity the transport member is preferably circular in cross section, for example a cylindrical feed barrel. However the transport member could have a sectional shape that is not circular, for example oval, square or triangular.

The sealing means may be provided on an external surface of the transport member, or separate sealing means may be provided that make a seal between the transport member and the housing or the stack of sensors. Where the seal is made with the housing, the opening in which the transport member is mounted must of course be the only opening to the inside of the housing. In a preferred embodiment the sealing means comprises a retractable shroud which surrounds the stack of sensors and which sealingly engages with the transport member when in an extended configuration. In another preferred embodiment, the sealing means is provided by a seal on a door which opens and closes the opening according to the rotational position of the transport member. The door may be provided with one or more teeth to restrain movement of the stack, and the transport member may be provided with one or more blades to take over the restraining function from the teeth when the door is open, prior to the recessed region of the transport member being brought into register with the stack. This embodiment has the advantage that the door may remain closed, and the seal intact, at all times except for the brief period when a sensor is being loaded and taken to the engagement location. The sealing means may be formed from any suitable material, for example natural or synthetic rubber.

The sensors may be conventional test strips of known construction. The invention will for convenience be described hereinafter with reference to test strips; however it is to be understood that other shapes of sensor could also be employed, for example square sensors or discs.

The invention provides a test device in which test strips are dispensed via a rotationally mounted transport member so that each test strip is conveniently brought to a location where it can engage with meter contacts and where it can receive a drop of fluid. Accordingly, another aspect of the invention provides a test device for testing of analyte concentration in a fluid to be applied thereto, comprising: a housing containing a stack of test strips and having an opening therein; a transport member rotatably mounted in the opening of the housing, having an axis of rotation which spans the opening; the transport member having a recessed region adapted to receive a single test strip; and spring means which urge the stack towards the transport member; wherein rotation of the transport member with a test strip in the recessed region thereof will bring the said test strip to an engagement location at which it can be engaged with electrical contacts of a meter and at which the test strip will be accessible to permit a user to apply a drop of fluid thereto.

In a preferred embodiment, each test strip comprises a base member having a working area to which the fluid is to be applied, containing the reagent means, and a non-working area adjacent to the working area, wherein the total thickness of the test member in at least a portion of the non-working area is at least as great as the total thickness of the test member in the working area.

By making the non-working area at least as thick as the working area, scuffing or abrasion of the working area in a stack can be reduced. Moreover, if a compressive load is applied to a stack of the test members, this may be spread out over a greater area, thereby reducing the possibility of compressive damage to the working area.

In a preferred embodiment, at least a part of the non-working area is of greater total thickness than the thickness of the working area. This further reduces the likelihood of damage to the working area by scuffing or abrasion when in a stack. The difference in thickness is preferably from 1 to 20 $\mu$m, notably from 5 to 10 $\mu$m.

To build up the working area, a plurality of layers are sequentially applied to the base layer, for example by screen printing, typically with curing or drying steps between the application steps. The layers which are printed typically comprise electrode patterns, a reagent layer, and a mesh layer (for spreading out an applied fluid). As a result of the application of these layers, the working area of a conventional electrochemical test strip is typically about 100 $\mu$m thicker than the non-working area, which contains the electrode tracks and, typically, a dielectric layer. A stack of 100 test strips will therefore be about 10 mm thicker in the working area than in the non-working area. In a test strip in accordance with the present invention, at least a part of the non-working area may be made thicker by any suitable means. Suitable means include, for example: a printed relief ink; an applied pad or tape; embossing of the base layer or an intermediate layer; or an extension of the mesh layer from the working area.

Further objects and advantages of the invention will be apparent as the description proceeds.

The term "spring means" is used herein for convenience. It will be understood that this term includes conventional springs and other biasing or urging means which perform an equivalent function; for example elastic or pneumatic biasing means.

DETAILED DESCRIPTION OF THE DRAWINGS

The invention will now be further described, by way of example, with reference to the following drawings in which.

Figure 8A:
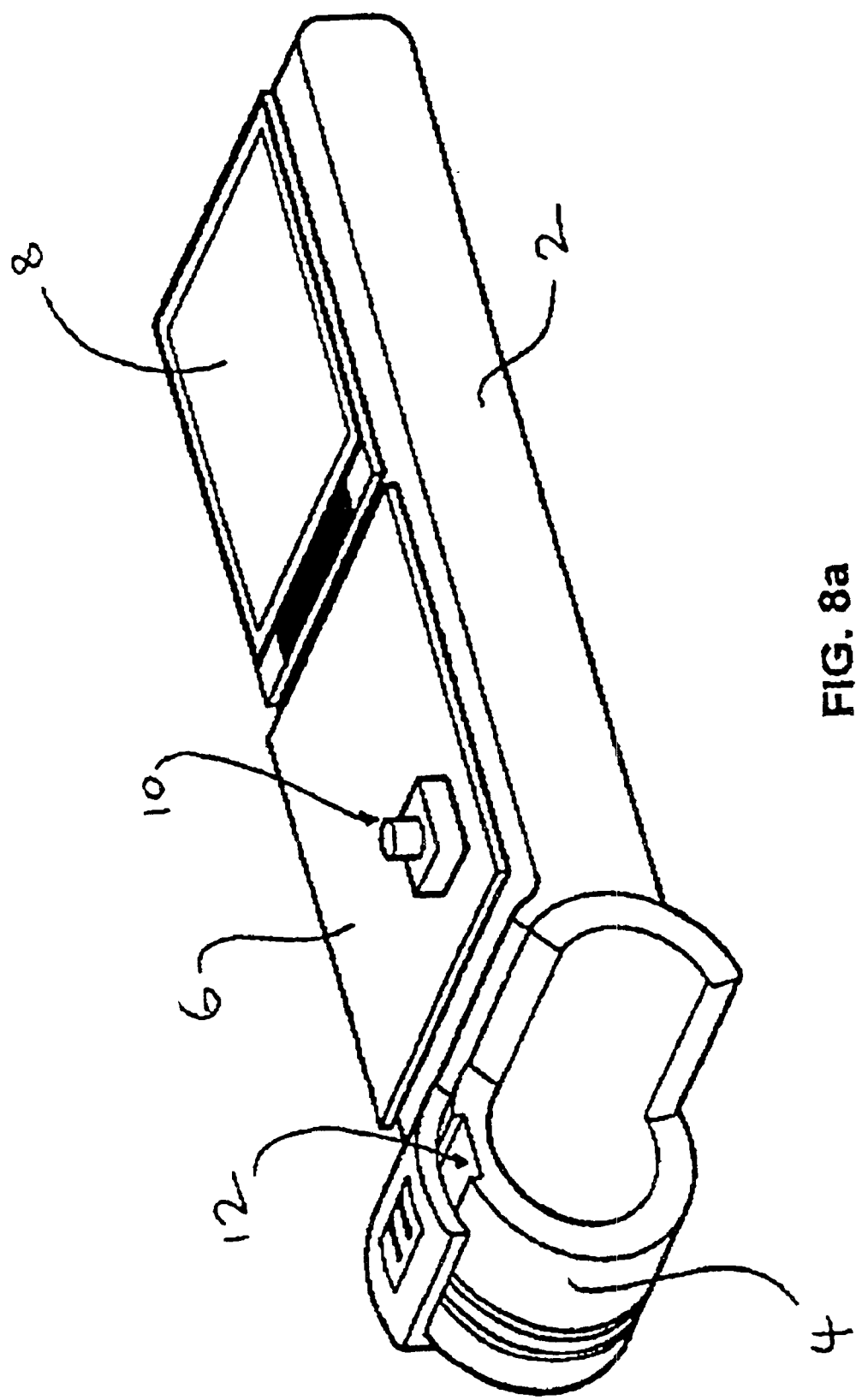
Figure 8B:
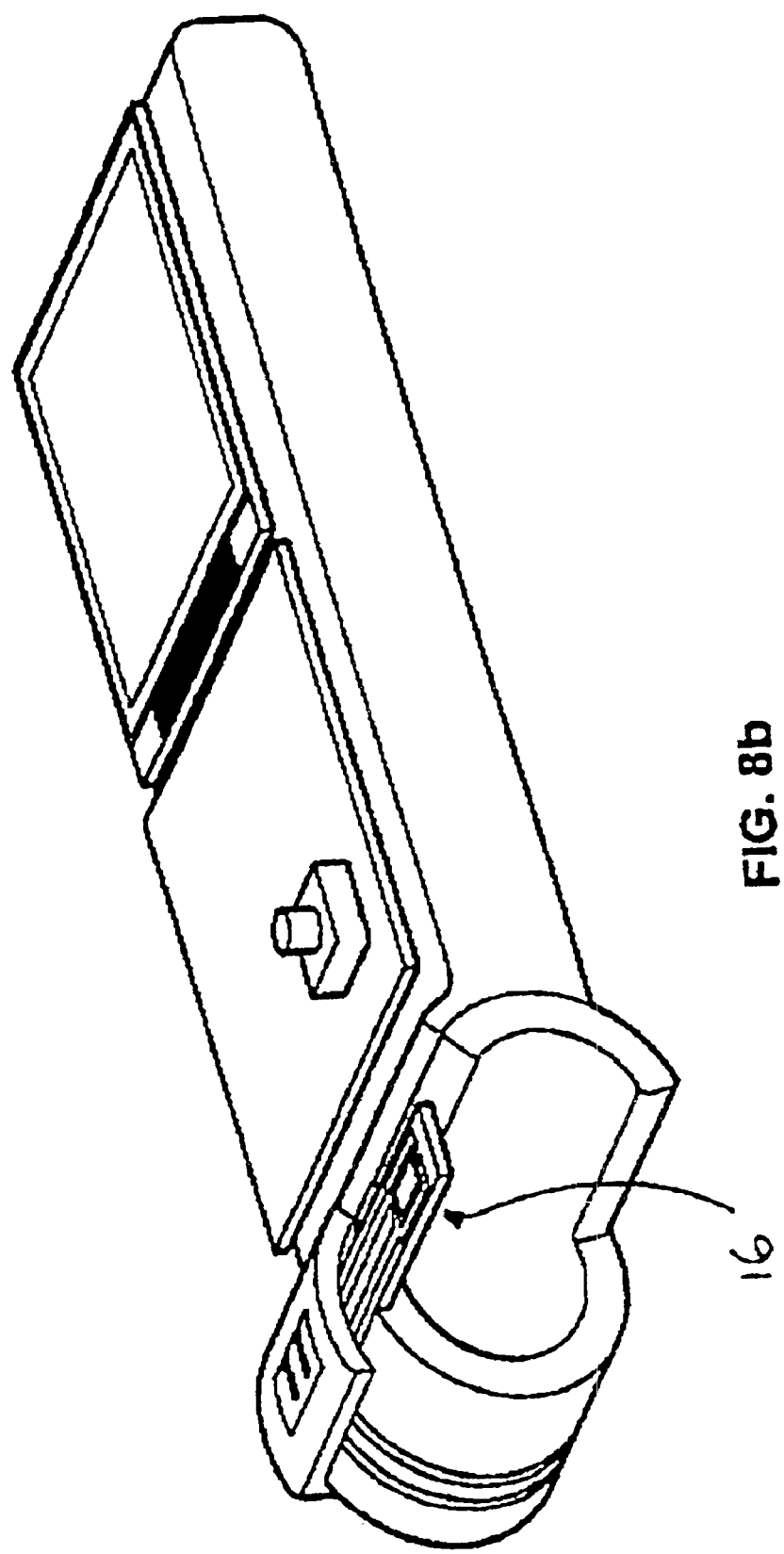
Figure 11:
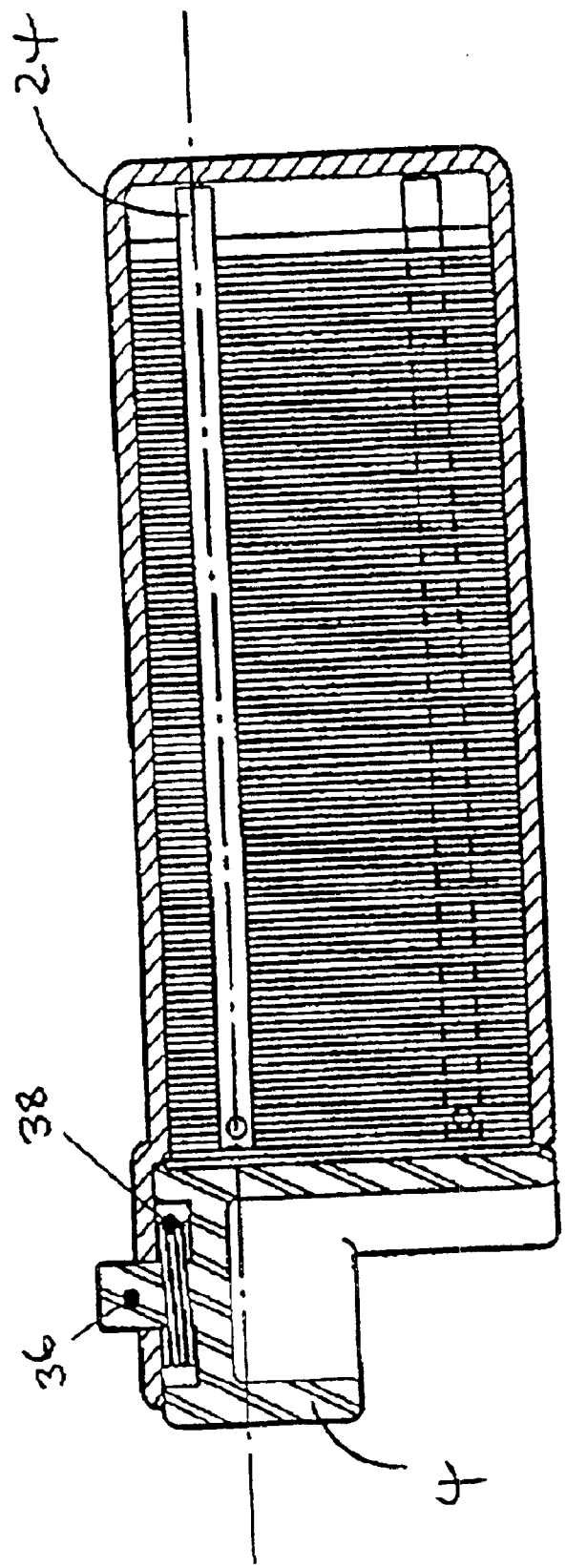
Figure 14A:
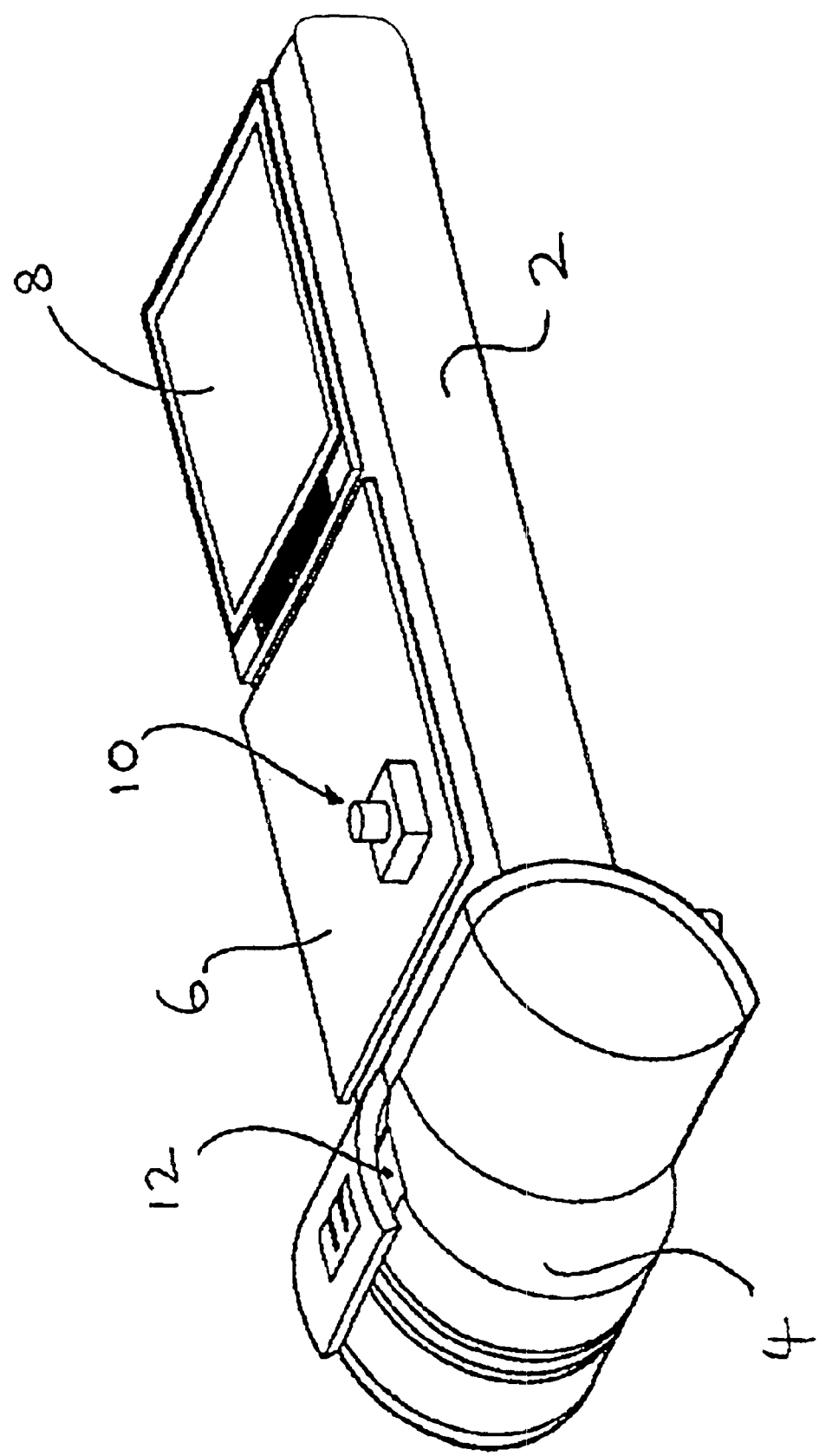
Figure 14B:
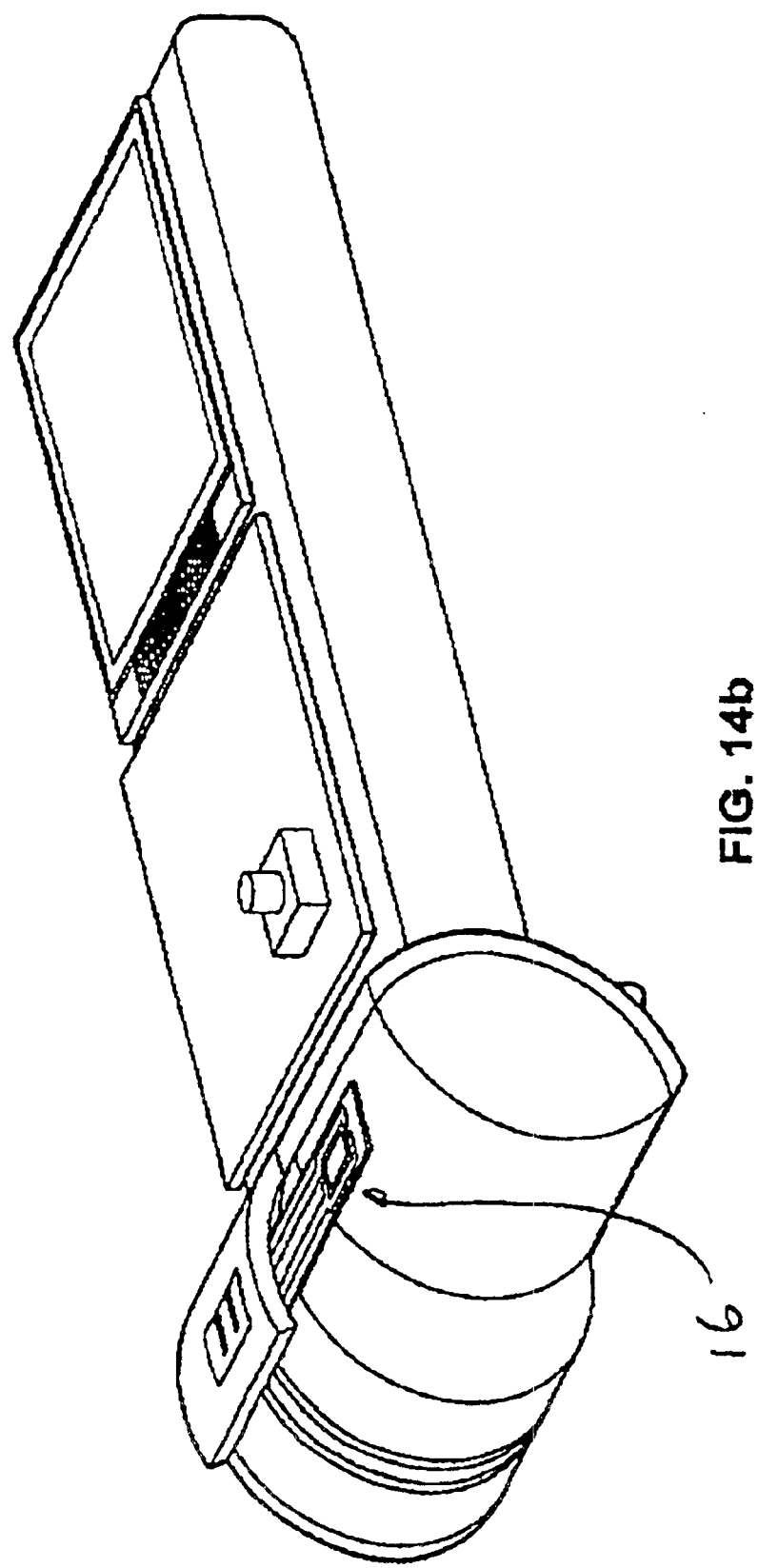

FIGS. 3(a–b) and 4(a–b) show vertical sectional views along the lines A—A and B—B respectively of FIG. 2;

FIGS. 5(a–c) and 6(a–c) show vertical sectional views corresponding to those of FIGS. 3 and 4 respectively, but with the transport member progressively rotated;

FIGS. 7(a–c) show respective sectional views along the lines E—E, F—F and G—G of FIGS. 5 and 6;

FIG. 8 shows perspective views of a test device in accordance with a second embodiment of the present invention;

FIG. 9 is a top plan view of the test device of FIG. 8a;

FIG. 10 is a sectional view along the line A—A of FIG. 9;

FIG. 11 is a sectional view along the line B—B of FIG. 10;

FIGS. 12(a–e) show sectional views corresponding to that of FIG. 10, with the transport member at different rotational positions;

FIGS. 13(a–c) show top plan views similar to FIG. 9, with a test strip in different positions during the course of a test measurement;

FIGS. 14(*a–b*) show perspective views of a test device in accordance with a third embodiment of the present invention;

FIG. 15 is a top plan view of the test device of FIG. 14*a;*

Figure 19A:
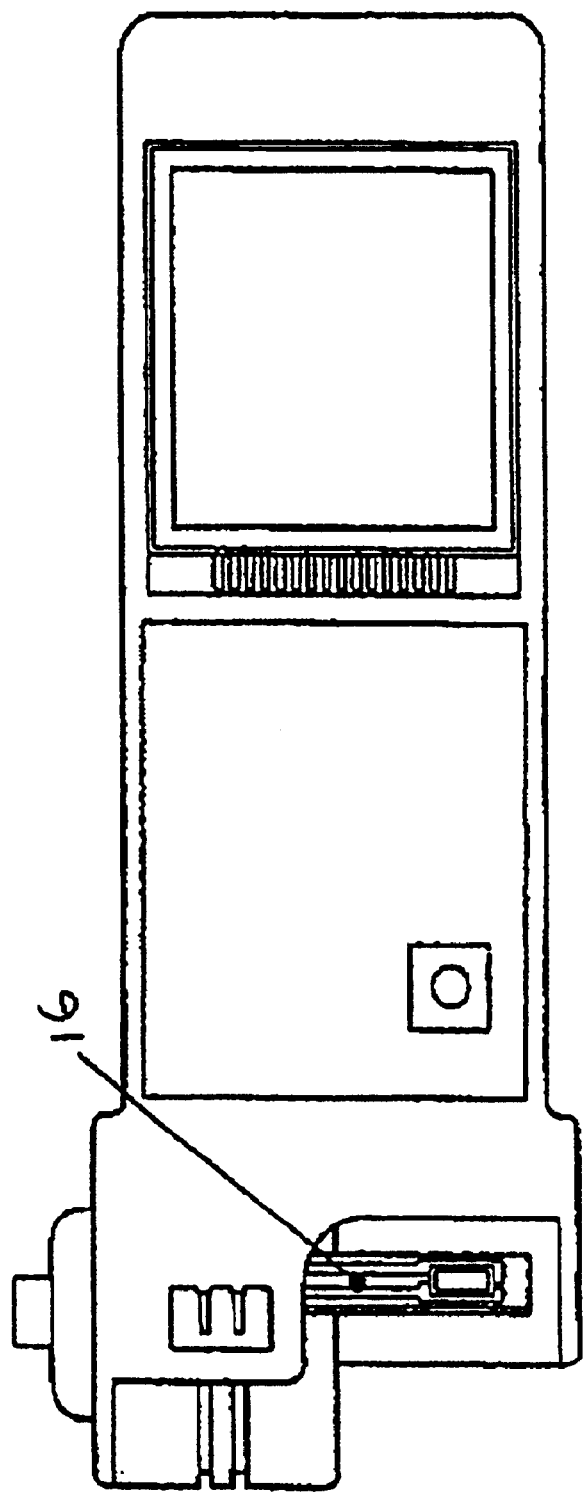
Figure 20:
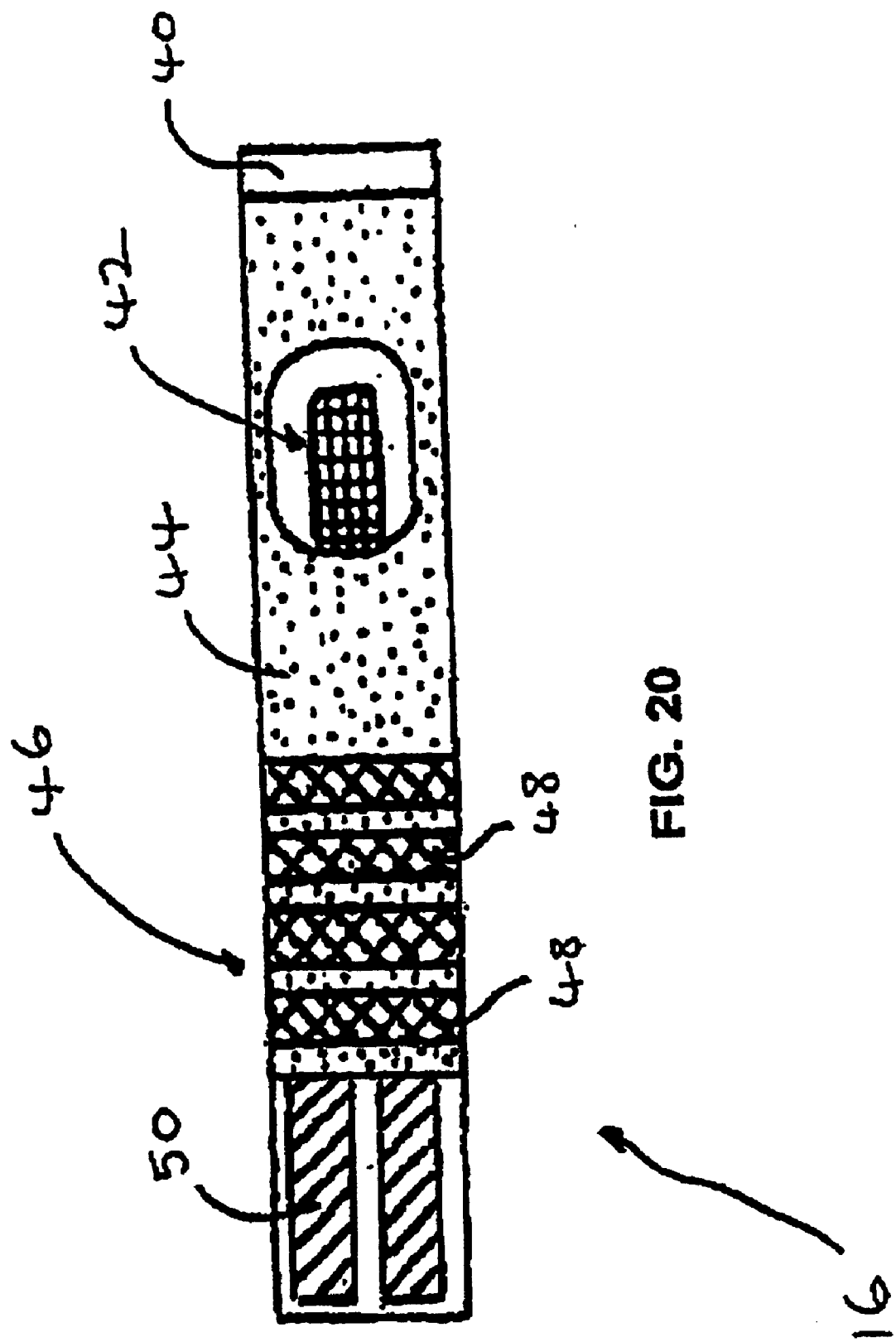
Figure 21:
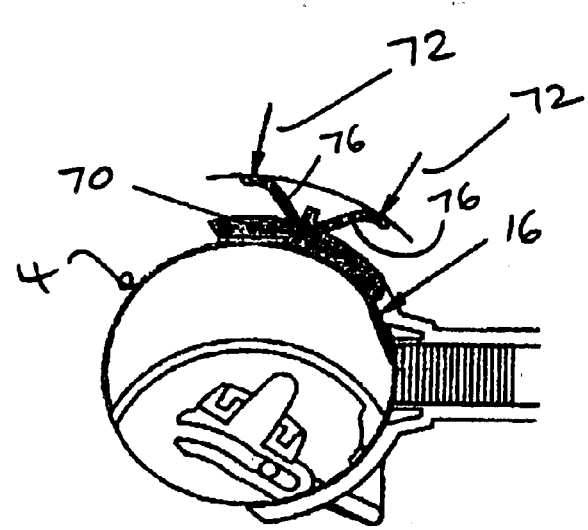

FIG. 16 is a sectional view along the line A—A of FIG. 15;

FIG. 17 is a sectional view along the line B—B of FIG. 16;

FIG. 18(*a–e*) show sectional views corresponding to that of FIG. 16, with the transport member at different rotational positions;

FIGS. 19(*a–c*) show top plan views similar to FIG. 15, with a test strip in different positions during the course of a test measurement;

FIG. 20 is a top plan view of a test strip in a preferred embodiment of the invention;

FIGS. 21 to 24 are sectional views through part of a further alternative embodiment, showing the operation of a sliding stop member;

FIGS. 25(*a–f*) show sectional views through a device in accordance with an embodiment of the invention, showing operation of a magazine ratchet mechanism;

FIGS. 26(*a–f*) show sectional views along the line A—A in FIG. 25;

FIGS. 27–28, 29(*a–c*) and 30–39 are perspective views showing a test device in accordance with another embodiment of the invention and its assembly.

DETAILED DESCRIPTION

In the embodiment illustrated in FIGS. 1 to 7, a test device for measuring glucose concentration in blood comprises a housing 2 which houses a stack of test strips 16 in a magazine 18. A transport member 4 (in this example, a feed barrel which is circular in cross section) is rotatably mounted in an opening of the housing 2 and has an axis of rotation which spans the opening. As will be described below, the teed barrel 4 has a recessed portion 12 which receives and transports a single test strip 16 from the stack in the magazine from a start position (FIG. 1*a*) to an engagement location (FIG. 1*b*) where electrode tracks 50 on the test strip engage with electrical contacts mounted in the housing and connected to a meter. With the test strip 16 in the engagement location a user can apply a drop of blood to the working area 42 of the test strip 16. The housing has mounted thereon a meter comprising a PCB 6 and display means B (in this example, an LCD) for displaying a readout of blood glucose concentration. Glucose concentration values from previous samples can be retained and displayed by operation of a memory button 10 on the PCB. Further rotation of the feed barrel 4 brings the used test strip 16 to an opening 14 in the housing 4 through which the test strip can be ejected or removed.

As shown in FIGS. 2 to 6, test strips 16 in the magazine 18 are protected by a moisture-proof retractable sealing member 20, which is tightly fitted around ribs 21 on the magazine 18. The free end of the retractable sealing member 20 is located in a groove 26 which surrounds the recess 12 where the test strip 16 is located in the start position. The retractable sealing member 20 is engaged by a movable support collar 22. In the start position, a constant tension magazine spring 24 urges the stack of test strips against the feed barrel 4 so that a single test strip 16 lies flat in the recess 12. Only a single spring is necessary, although an optional second spring is also illustrated.

Figure 1A:
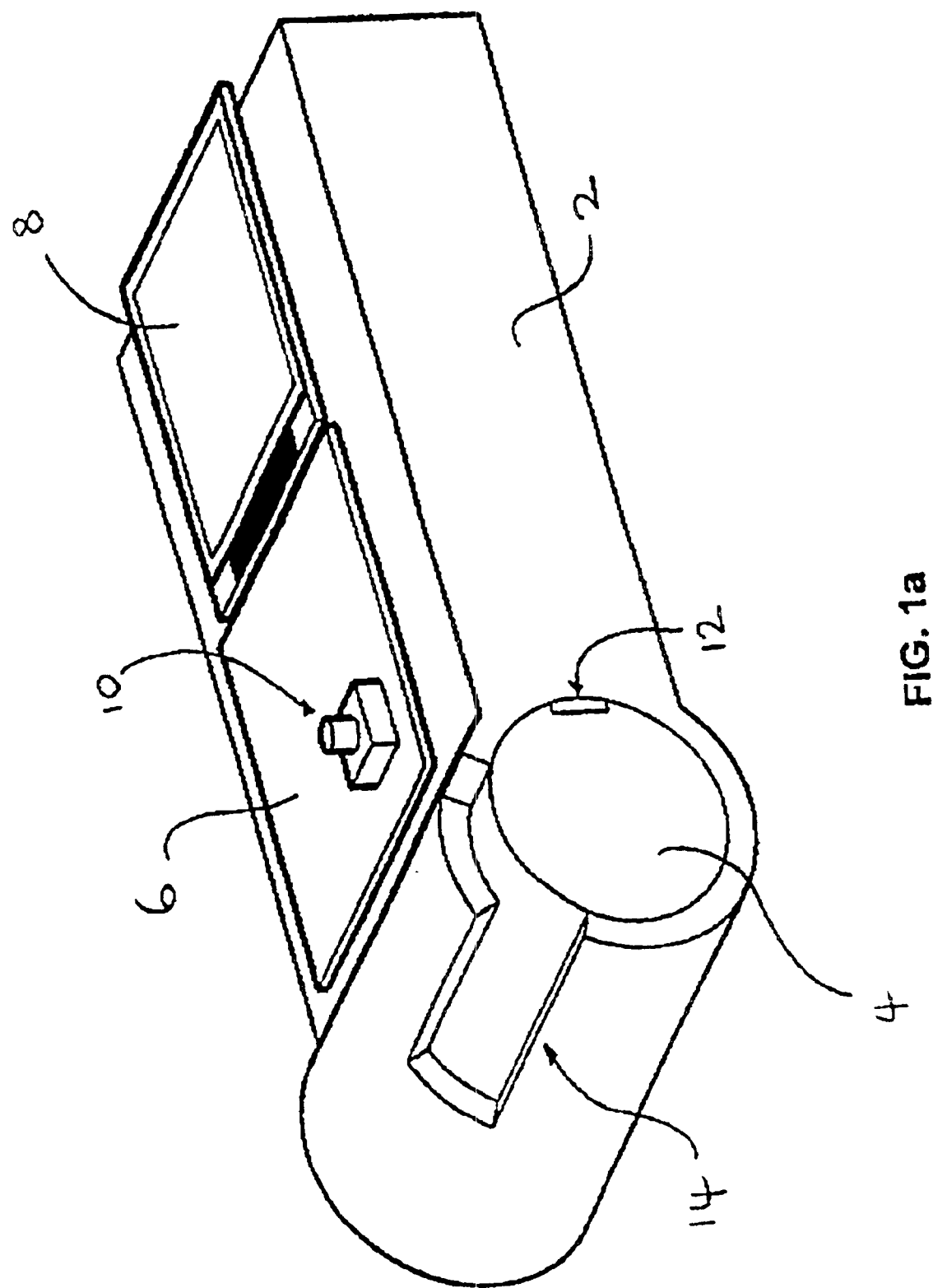
FIGS. 1(a–b) show perspective views of a test device in accordance with a first embodiment of the present invention.
Figure 1B:
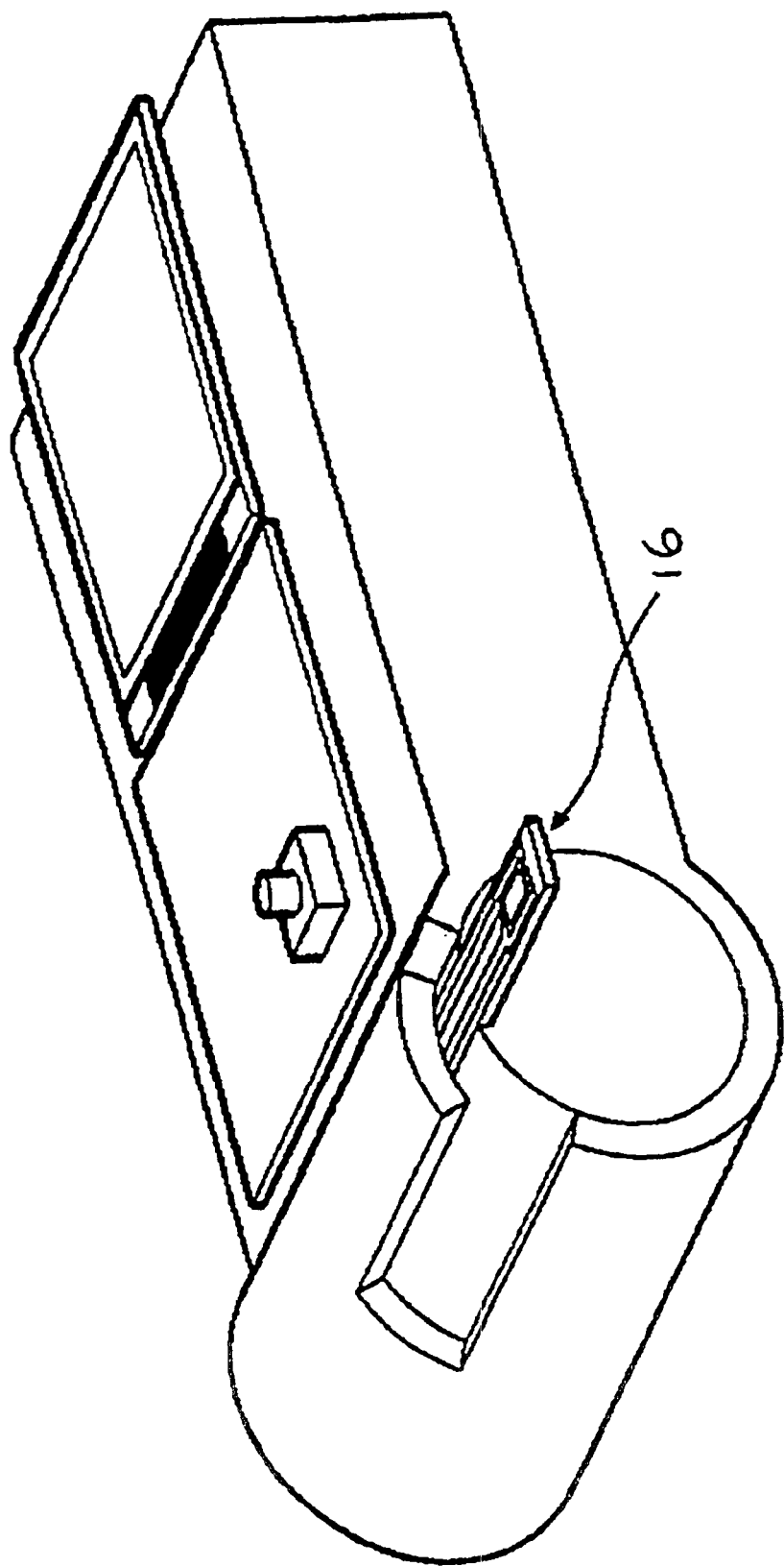
Figure 2A:
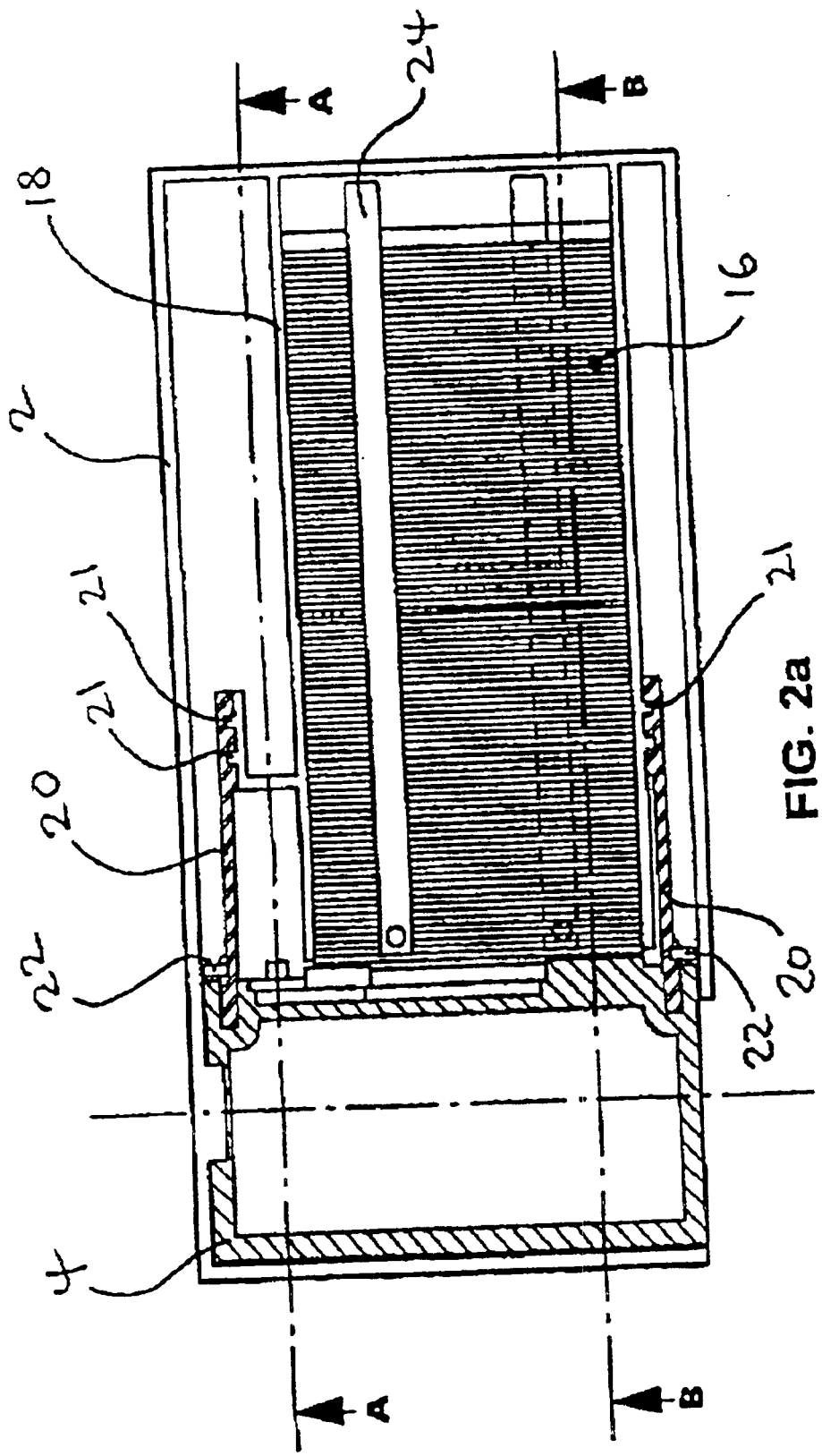
FIGS. 2(a–b) show horizontal sectional views through the device of FIG. 1a, along the line C—C of FIG. 4) with the sealing means extended and retracted.
Figure 3B:
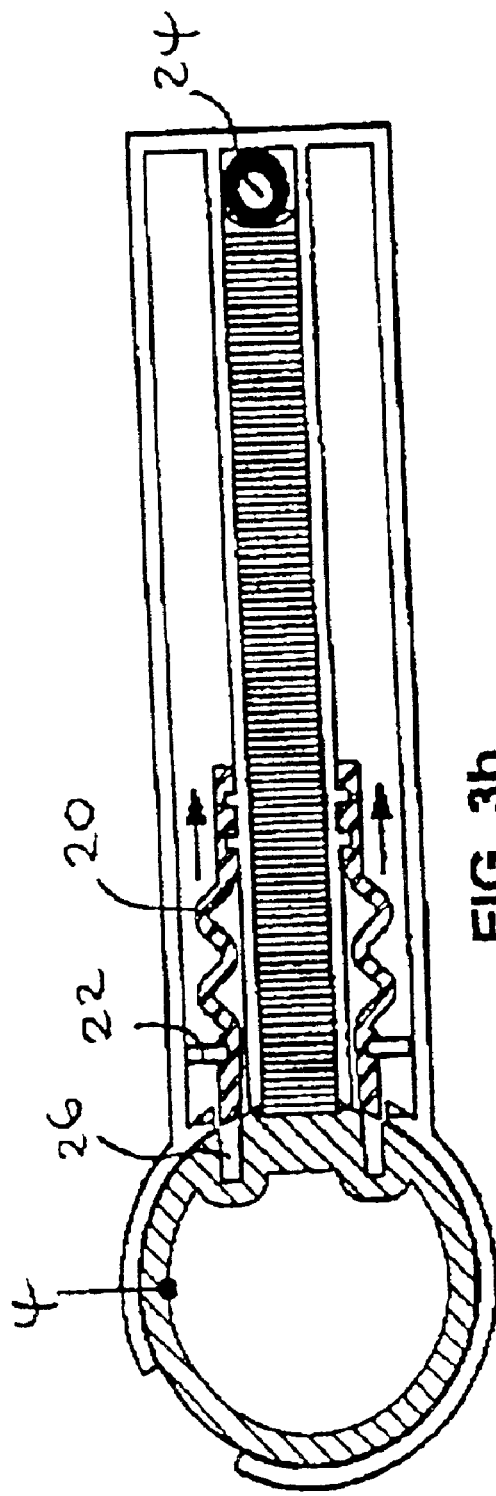
Figure 4B:
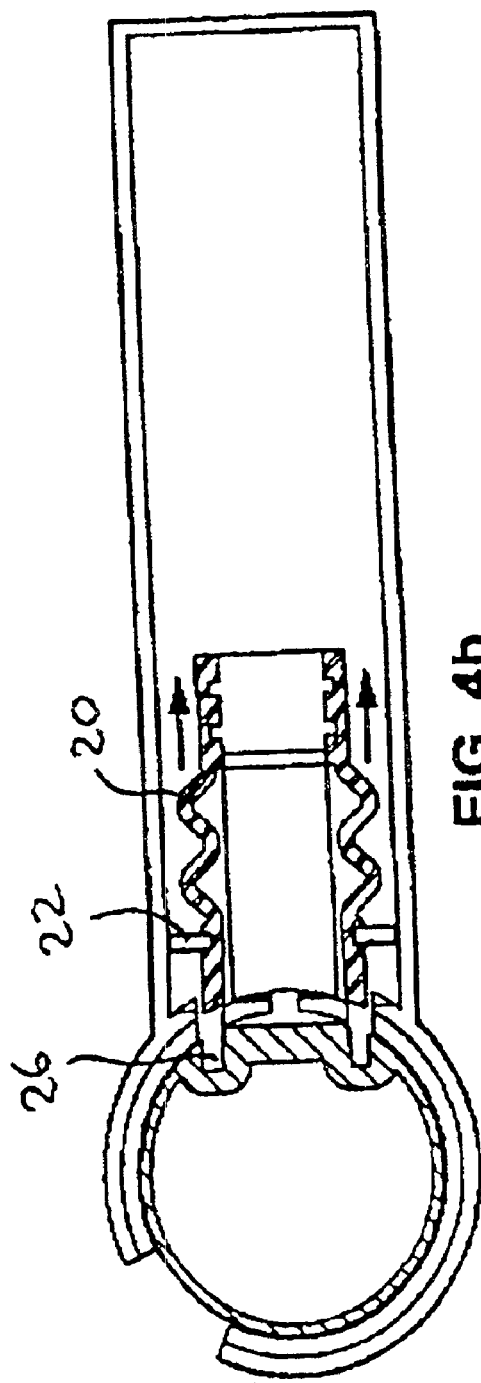

When the user initiates turning of the feed barrel 4 in the start position (FIGS. 2*a*, 3*a*, 4*a*), the first thing that happens is that the support collar 22 is moved away from the feed barrel 4 so as to disengage the free end of the retractable sealing member 20 from the groove 26, thereby permitting rotation of the feed barrel 4 (FIGS. 2*b*, 3*b*, 4*b*).

Figure 6B:
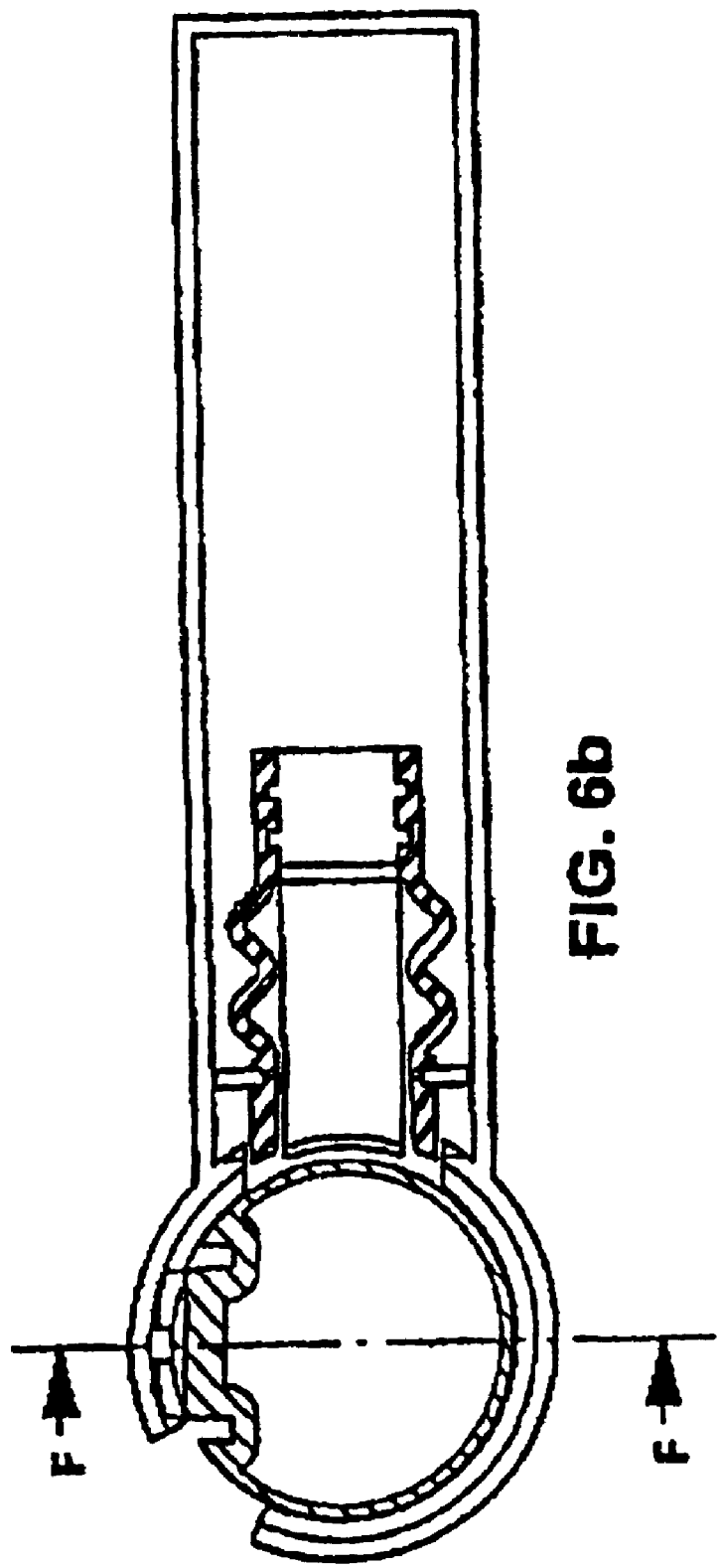

With the retractable sealing member 20 in a retracted configuration, the feed barrel 4, carrying a single test strip 16, is turned by the user (FIGS. 5*a*, 6*a*) until the test strip 16 is at the top of the feed barrel 4, as shown in FIGS. 5*b* and 6*b*. At the same time, a captured pusher 28, behind the test strip 16, engages a helical track 30 (FIGS. 7*a*, 7*b*) in the housing 2. This track 30 moves the pusher 28 forward which in turn moves the test strip 16 out of the housing 2 and into the engagement location. As the test strip 16 reaches the engagement location, it flexes a contact (not shown) into a "wake up" position which activates the meter into a ready for use state. The feed barrel 4 is turned against a return spring (not shown). In the engagement location, the barrel 4 is held by a "ball point pen" type mechanism (not shown). After a reading has been taken, further turning of the feed barrel 4 (FIGS. 5*c*, 6*c*, 7*c*) brings the recess 12 and used test strip 16 to the opening 14 where the test strip 16 may drop out or urged out by ejection means. On release of the feed barrel 4 from the exit location, the return spring returns the feed barrel 4 to the start position, where the next test member 16 from the stack engages in the recess 12. The process can then be repeated until all test members have been used up. The device may then be discarded.

In the embodiments shown in FIGS. 8 to 19, parts with similar structure and function to the first embodiment are given the same reference number.

In the second embodiment shown in FIGS. 8 to 13, the feed barrel 4 is partially cutaway so that a test strip 16 is only partially supported in the recess 14. The part of the housing 2 in which the feed barrel 4 is mounted is also cutaway, so that a used test strip which is turned so that it exits the housing can drop out or be ejected. A seal 34 is provided on part of the full length outer surface of the feed barrel 4 so that, in the start position illustrated in FIGS. 8*a* and 9 to 11, the seal 34 creates a moisture tight seal between the test strips 16 and the feed barrel 4.

From the start position, a user brings a test strip 16 to the engagement location where it engages with electrical contacts 32 on the housing 2 by the steps illustrated in FIGS. 12*a* to 12*d*, 13*a* and 13*b*. The feed barrel 4 is provided with a drive axle 36. The user turns the drive axle 36 in the direction of the arrow as shown in FIG. 12*a*, against the force of a return spring 38, to the feed position shown in FIG. 12*b*. Here the recess 12 is brought into register with the test strips 16, and a single test strip 16 locates in the recess 12. The user then releases the drive axle 36, and the return spring 38 carries the feed barrel 4 back to the start position via the intermediate position shown in FIGS. 12*c* and 13*a*. With the electrode tracks on the test strip 16 engaged with the electrical contacts 32 of the meter, the user now takes a reading of blood glucose concentration. The seal 34 once again seals off the test strip cartridge from atmospheric moisture, so that test strips in the cartridge are protected from moisture while the reading is being taken.

After the reading has been taken, the user turns the drive axle 36 in the direction of the arrow 35 (FIG. 12*e*) and the used test strip 16 is either permitted to drop from the recess 12 or is positively ejected (FIGS. 12*e*, 13). The user then releases the drive axle 36 and the feed barrel is returned to the start position by the return spring 38. The cartridge of test strips is kept sealed from moisture at all times except for short periods when a test strip is being loaded and when the used test strip is being ejected.

Turning now to FIGS. 14 to 19, the third embodiment illustrated is similar to the second embodiment, but includes special means for retaining sensors in the magazine and for sealing the magazine even during ejection of a used test strip.

Figure 18C:
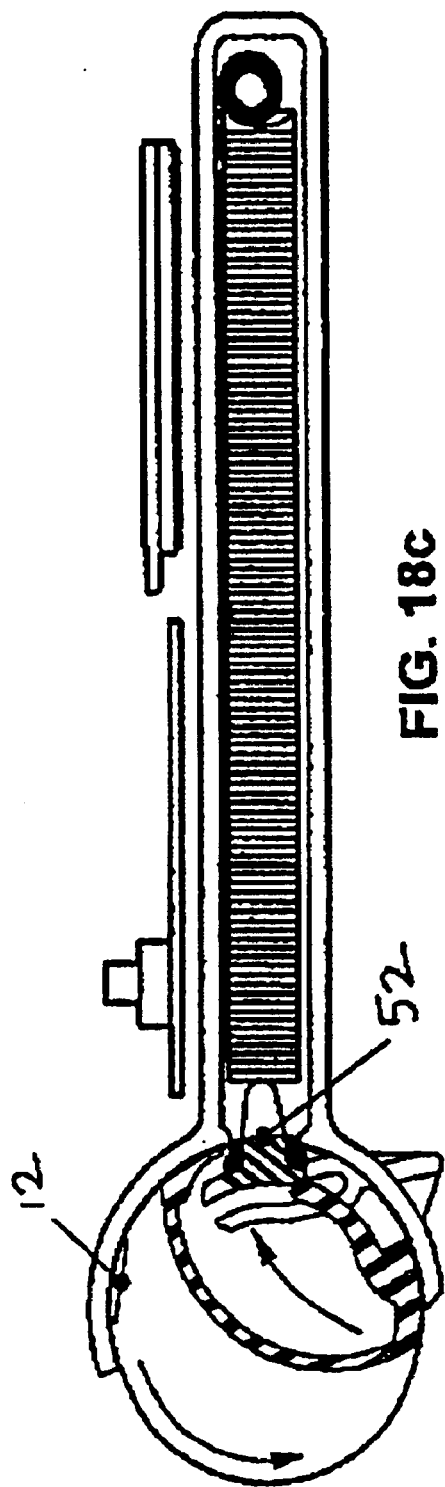

The feed barrel 4 is provided with a separate magazine door 52 which has a door seal 66. When the door 52 is closed, the door seal 66 protects test strips 16 from atmospheric moisture. A plurality of fingers 54 are provided on the door, and these fingers keep the test strips 16 away from the door seal 66. The door 52 is pivotally mounted to a pivot point 56, and is provided with arms 58. Pulling or pushing on an arm 58 causes pivoting of the door 52. Within the feed barrel 4 there is provided an actuating member 60 which includes a pair of spaced apart arms 68 and a pair of spaced apart fingers 64. The end of each finger 64 is journalled between a pair of arms 58 on the magazine door 52. At the end of each arm 68 of the actuating member there is provided a blade 62. To take a blood glucose reading, the following actions are performed. From the start position shown in FIG. 16, the user turns the feed barrel 4 in the direction of the arrow shown in FIG. 18a. The actuation member 60 also turns, and the fingers 64 pull on an arm 58 of the magazine door 52. The door 52 pivots and begins to withdraw from the magazine. The stack of test strips 16 follows, urged by the spring 24 and restrained by the teeth 54. At the same time, the blades 62 are rotated so that they lie between the teeth 54 and take over the job of restraining the test strips 16 (FIG. 18a). As the feed barrel 4 is further rotated (FIG. 18b) the blades 62 move out of line with the magazine opening and the recess 12 on the feed barrel moves into alignment with the test strips 16. A single test strip 16 lies flat in the recess 12. The user then permits the return spring 38 to turn the feed barrel 4 in the direction of the arrow shown in FIG. 18c, so as to bring the test strip 16 in the recess 12 to the engagement location (FIG. 18d). As the barrel 4 turns, initially the blades 62 and subsequently the teeth 54 push the stack of test strips 16 further back into the magazine. The magazine door 52 is closed again and the door seal 66 again seals the inside of the magazine from moisture. After a test reading has been taken, the user turns the feed barrel in the direction shown by the arrow in FIG. 18e, and the used test strip is discarded. During testing and during discarding of the test strip, the door 52 remains closed by virtue of lost motion between the fingers 64 on the actuating member 60 and the arms 58 of the door 52. On release of the drive axle 36, the return spring 38 restores the device to the start position and the process can begin again.

Figure 22:
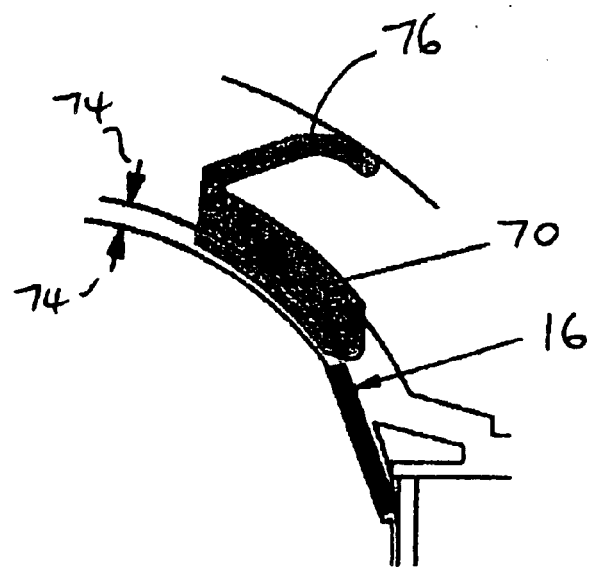

Referring now to FIGS. 21 to 24, an embodiment is illustrated in which a sliding stop member 70 is provided to help compensate for bowed strips 16. The sliding stop member 70 is provided between the outer surface of the feed barrel 4 and the outer wall of the meter. As the barrel 4 rotates anti-clockwise, bringing a test strip 16 out of the magazine, the leading edge of the stop member 70 is lifted by the edge of the strip 16. As the barrel 4 rotates the strip 16 pushes arms 76 of the sliding stop 70 up against the outer wall creating a low spring force applied to the edges of the strip. The spring force (in the direction of arrows 72) presses the strip 16 down against its recess in the barrel 4 to prevent bowed strips from sticking or jamming the mechanism during use. FIG. 22 shows the lead-in 74 designed into the leading edge of the sliding stop 70. The height of the lead-in from the base of the strip recess in the barrel is 1.2 mm. The strip thickness is 0.63 mm (averaged over 50 strips); this means that the sliding stop mechanism can compensate for a maximum strip bow of 1.2−0.63=0.57 mm. We have found that typically test strips will have a maximum bow of 0.13 mm.

Figure 23:
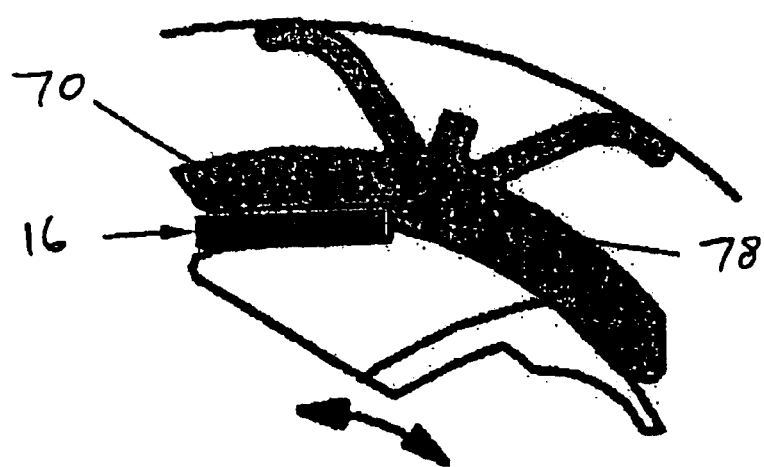
Figure 24:
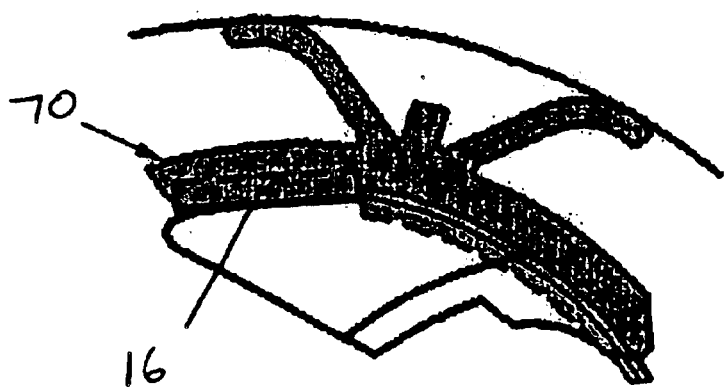

FIG. 23 shows the location of the test strip 16 while in use. The strip 16 is located horizontally under the contacts and held in place by the stop member 70. Built into the stop member 70 is a non-return feature 78 that springs down as the strip 16 reaches the engagement location. If the user accidentally turns the barrel 4 in the wrong direction (ie, rotating the barrel to the test member pickup position instead of the eject position) the barrel 4 is free to rotate, which prevents damage to the mechanism, but the test strip 16 will be prevented from moving by the non-return feature 78. This helps prevent contamination of unused test strips with blood from the used strip. Referring now to FIG. 24, when the test strip 16 has been ejected, the sliding stop member 70 is in its rest position in a recess in the barrel 4. In this position it covers the front of the electrical contacts preventing ejected strips from being re-inserted into the meter.

Test strips 16 in the magazine 18 are urged towards the transport member 4 by a follower 80 which is acted on by spring means 24. It is desirable to reduce the backward movement of the follower in the magazine sub-assembly to a distance which is too small to permit the test strips 16 to flip over. A magazine ratchet mechanism to achieve this is illustrated in FIGS. 25 and 26. FIGS. 25a and 26a show sections through a magazine 18 which has a stack of test strips 16 of which about half have been used and ejected. The stack is urged by a follower 80 towards the door 52 by a spring (not shown). The follower 80 is provided with a pair of pivotally mounted pawls 82, each of which is engaged in a herringbone ratchet track 84.

Turning to FIGS. 25b and 26b, retraction of the hinged door 52 permits the stack of test strips 16 and the follower 80 to advance. The twin pawls 82 accommodate the advance of the follower 80 by rotating to the outer edge of the herringbone track, and a test member 16 is extracted from the top of the stack and presented for use. After the test strip 16 is extracted (FIGS. 25c and 26c), the door 52 is closed and pushes the test member stack and follower 80 down the magazine 18. The right hand pawl 82 prevents the follower 80 from travelling down the magazine 18 because the end of the pawl 82 can go no further than the end of the "bone" of the herringbone track in which the pawl is engaged. Moreover, the side 86 of the follower 80 adjacent the right hand pawl 82 limits rotation of that pawl and so the downward travel of the follower 80.

Figure 25F:
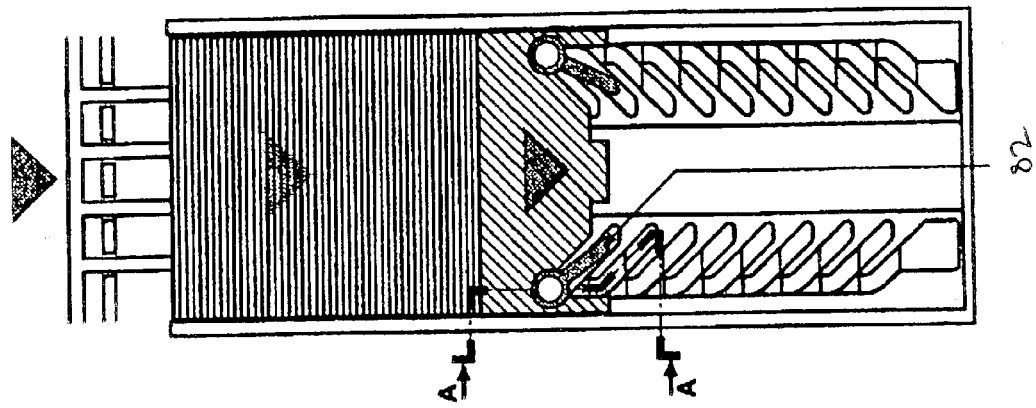
Figure 26F:
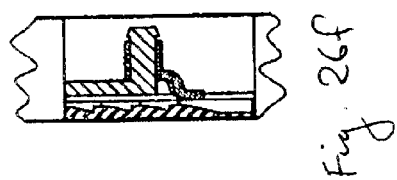
Figure 25E:
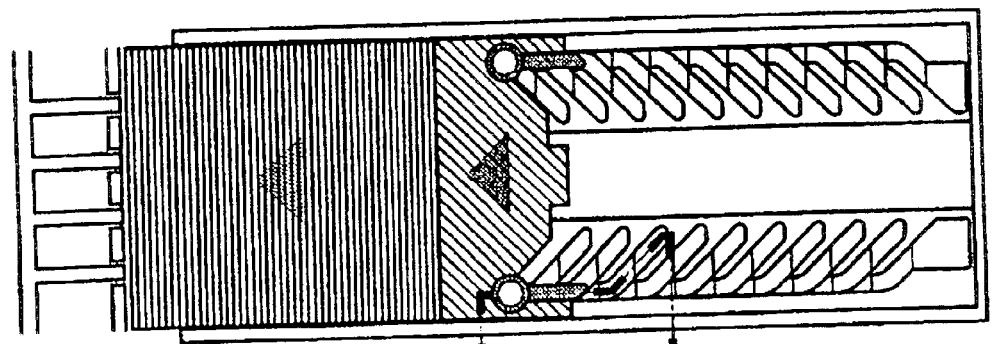
Figure 26E:
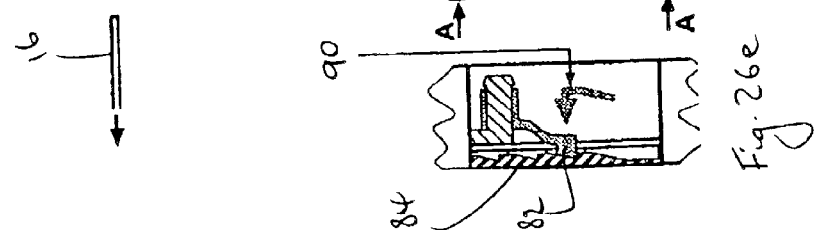

FIGS. 25d and 26d show the situation after about seven test strips 16 (dependent on strip thickness) have been extracted since FIGS. 25c and 26c. The gap 88 represents the longest downward travel the follower 80 is allowed to make before the left hand pawl 82 is snapped into a new herringbone track. Turning now to FIGS. 25e and 26e, a further test strip 16 is extracted, permitting the left hand pawl 82 to move over the separating wall between two herringbone ratchet tracks so that it snaps down into the next track. The left hand pawl 82 is now the limiter of downward movement for the follower 80 (FIGS. 25f and 26f) until a further seven test strips 16 have been extracted when the right hand pawl will again take over.

Referring now to FIGS. 27 to 39, a further alternative embodiment of the invention, and its assembly, is described. The test device has a handle 92 for turning the transport member 4 (best shown in FIG. 30) and a slot 94 in its external housing to permit presentation of a test strip. A clip-on dust sleeve 96 covers the slot 94 when the device is not in use.

Operation of the device by a user is illustrated in FIG. 29. The user pivots the handle 92 upwards (FIG. 29a) causing a test strip 16 to be picked up by the transport member. When the handle 92 is returned to its rest position (FIG. 29b) a test strip 16 passes through the slot 94 and is presented for use. After a reading has been taken, the handle 92 is turned again (FIG. 29c) in the opposite direction to its initial turning, to release the used test strip 16. After the handle is returned to the rest position the device is ready for use again.

An exploded diagram of the component parts of the device is shown in FIG. 30, and their assembly is shown in the subsequent figures. The magazine (first) subassembly 112 comprises the magazine 18 with a stack of test strips therein, the follower 80 and a constant tension spring 24 operatively attached thereto. The magazine subassembly 112 is mounted in the magazine housing member 110. The door 52 and associated seal is pivotally mounted to the magazine housing member 110 by means of pivot pins 114 on the door 52 that are a snap fit for resilient brackets 108 on the magazine housing member 110, as best shown in FIGS. 31 and 32. The door is spring biased by return springs 106.

Figures 33, 34:
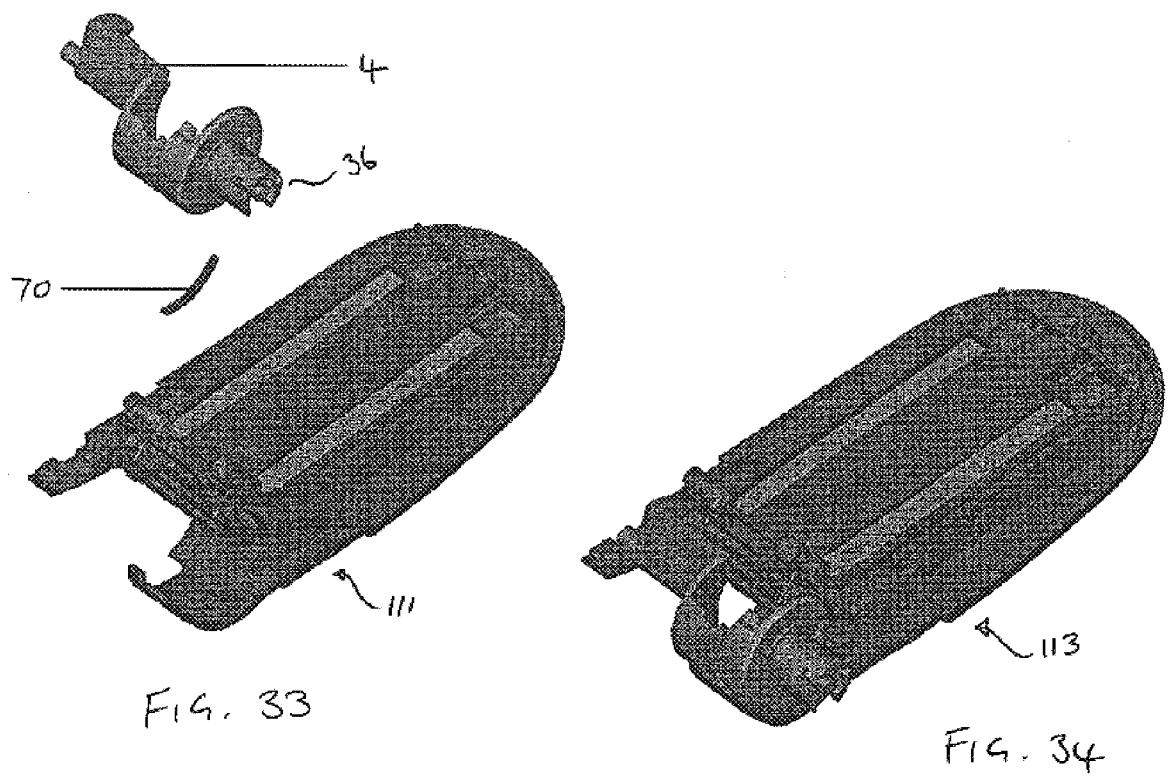
Figure 39:
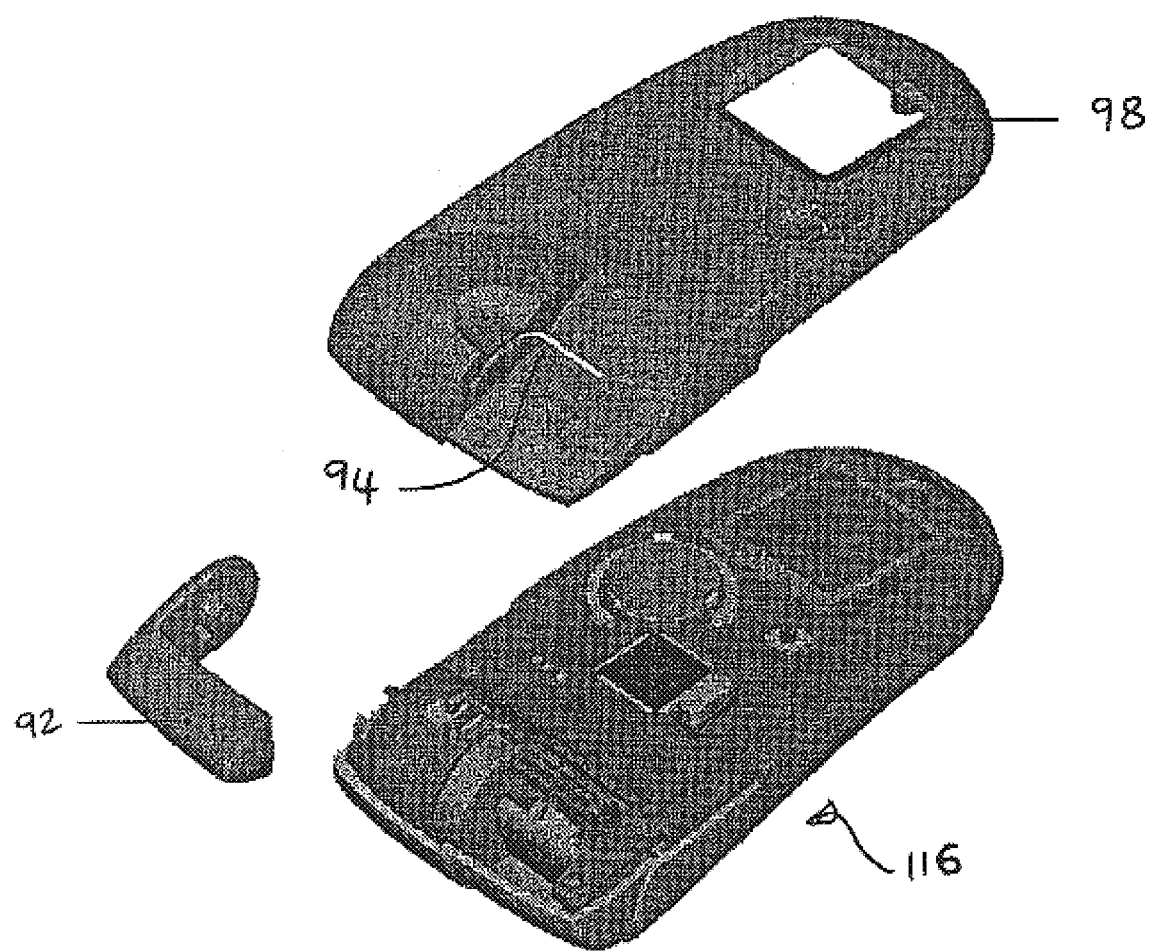

To the resultant door and magazine (second) subassembly 111 is mounted the transport member 4 as best shown in FIG. 33. The sliding stop member 70 is mounted between the transport member 4 and the corresponding portion of the magazine housing member 110. This third subassembly 113 is shown in FIG. 34.

The third subassembly 113 is then turned over (from the view shown in FIG. 34) and secured to the bottom of the housing 2. A gasket 102 is provided in the bottom of the housing 2 to make a seal around the magazine subassembly 112. Stakes 104 are provided on the housing 2 and the magazine housing member 110 which are ultrasonically welded together during assembly of the test device to produce a fourth subassembly 115. Sensor contacts 32 are located appropriately on the fourth subassembly, and the PCB 6 is then mounted on the fourth subassembly 115 so as to retain the sensor contacts 32 in electrical contact therewith. The PCB 6 is provided with appropriate electronics, an LCD 8, battery 100 and memory button 10.

To the resulting final (fifth) subassembly 116 is added a clip-on cover 98, clip-on dust sleeve 96, and the handle 92, which is a push fit for the drive axle 36. A barrel return spring 38 is mounted between the handle 92 and the magazine housing 110 to bias the handle to the rest position shown in FIG. 28.

The test strip 16 shown in FIG. 20 comprises a planar base member 38, in this example of poly(butylene terephthalate) (PBT) (Valox® FR-1 from GE Plastics). The strip is 30 mm×5.5 mm, and 0.5 mm thick. A working area 40 is of conventional construction, comprising a plurality of electrodes, a reagent layer in intimate contact with the electrodes, and a mesh layer for spreading out a drop of fluid to be received on the working area. Electrode tracks 48, for example of carbon, in the non-working area 44 of the test strip are connected to the electrodes in the working area 40 in known manner. Also in known manner, a dielectric layer 42 is printed around the working area 40 so as to overlie a portion of the electrode tracks 48, leaving just the ends of the tracks exposed for connection to corresponding electrodes 32 on the meter. The layers are applied to the base member as inks, by screen printing. Each ink layer is about 10 to 20 $\mu$m thick, and the mesh is about 59 to 67 $\mu$m thick. The working area 40 has a total thickness which is about 100 $\mu$m thicker than the non-working area 44 up to the dielectric layer 42.

To increase the thickness of parts of the non-working area, a high relief ink 46 has been printed in four strips. The high relief ink has a dried thickness such that the total thickness of the non-working area to which the high relief ink 46 has been applied is slightly greater than the total thickness of the test strip in the working area 40. Thus, when a stack of such test strips 16 is formed, and a compressive load is applied to the stack by the spring 24, the working area 40 will not bear all the compressive load. Scuffing of the test area will be reduced compared to a conventional test strip in which the working area stands proud of the non-working area.

Although this embodiment has been illustrated with reference to the use of a high relief ink printed in strips, it will be understood that it is not limited to this embodiment. The ink could be printed as a continuous block, and it could entirely surround the working area if desired. Instead of, or in addition to, the high relief ink, other means could also be provided to increase the thickness of the non-working area, for example: an applied pad or tape; embossing of the base layer or an intermediate layer; or an extension of the mesh layer from the working area into the non-working area.

It is appreciated that certain features of the invention, which are for clarity described in the context of separate embodiments, may also be provided in combination in a single embodiment. Conversely, various features of the invention which are, for the sake of brevity, described in the context of a single embodiment, may also be provided separately or in any suitable subcombination.

Although the invention has been described with reference to a test device for measuring blood glucose concentration, it is to be understood that the invention is not limited to this application. The invention may be used in the determination of any analyte in a fluid by the use of suitable reagents in the test strip. Such reagents are well known to those skilled in the art.

What is claimed is:

1. A test device for testing of analyte concentration in a fluid to be applied thereto, the device comprising:

a) a plurality of sensors arranged in a stack, each of said sensors carrying reagent means for producing an electrical signal in response to the concentration of analyte in an applied fluid, each of said sensors having a plurality of electrode tracks for transmitting said electrical signal;

b) a housing having an opening therein and containing the said stack of sensors;

c) electrical contacts mounted in relation to the housing for engaging with electrode tracks on a sensor at an engagement location;

d) a meter connected to the said electrical contacts, having electronics means for producing a signal output which is dependent on the electrical signal from a sensor when the sensor is engaged with the said contacts;

e) a transport member rotatably mounted in the opening of the housing, having an axis of rotation which spans the opening and having an outer surface which is provided with a recessed region adapted to receive a single sensor from the stack;

f) spring means within the housing which urge the stack of sensors towards the transport member and which urge a single sensor into the said recess when the recess is suitably aligned adjacent to the stack;

g) sealing means for making a moisture tight seal between the transport member and the stack when the transport member is in a specified rotational position; and h) wherein rotation of the transport member with a sensor in the recessed region will transport the sensor to the engagement location or to a position where the sensor can be moved to the engagement location, whereby electrode tracks of the sensor can engage with the said electrical contacts.

2. A test device as claimed in claim 1, wherein the sensors are stacked in a magazine within the housing, the magazine having a single opening which faces the transport member.

3. A test device as claimed in claim 2, wherein a first end of the sealing means forms a seal around the magazine and a second end of the sealing means locates in a groove in the transport member to form a seal therewith when the recessed region of the transport member is in register with the stack of sensors.

4. A test device as claimed in claim 3, wherein the sealing means comprises a retractable sleeve which sealingly engages in the groove of the transport member when in an extended configuration and which does not form a seal with the transport member when in a retracted configuration.

5. A test device as claimed in claim 1, wherein a pusher is provided to impart translational motion to a sensor mounted in the said recessed region during and/or after rotation of the transport member so as to bring the sensor to the engagement location.

6. A test device as claimed in claim 5, wherein the pusher is mounted on the transport member and a portion of the pusher is located in a helical track in the housing whereby rotation of the transport member imparts translational motion to the pusher.

7. A test device as claimed in claim 1, wherein the said opening is the only opening to the inside of the housing, and wherein the sealing means comprises a seal which is secured in relation to an outer surface of the transport member and which seals the opening of the housing when the transport member is in a specified rotational position.

8. A test device as claimed in claim 2, wherein the sealing means comprises a seal which is secured in relation to an outer surface of the transport member and which seals the opening of the magazine when the transport member is in a specified rotational position.

9. A test device as claimed in claim 1, wherein the said opening is the only opening to the inside of the housing, and wherein the sealing means comprises a seal provided on a door which is adapted to fit the said opening so that the moisture tight seal is effected by closure of the door; wherein the door is operatively connected to the transport member so that the door will be open when the transport member is in a first rotational position and closed when the transport member is in a second rotational position.

10. A test device as claimed in claim 2, wherein the sealing means comprises a seal provided on a door which is adapted to fit the opening of the magazine so that the moisture tight seal is effected by closure of the door; wherein the door is operatively connected to the transport member so that the door will be open when the transport member is in a first rotational position and closed when the transport member is in a second rotational position.

11. A test device as claimed in claim 9, wherein the door is provided with one or more teeth which restrain movement of the stack of sensors against the force of the spring means.

12. A test device as claimed in claim 11, wherein the transport member is provided with at least one blade which takes over the function of restraining the stack of sensors when the door is opened.

13. A test device as claimed in claim 9, wherein the door is pivotally mounted in relation to the housing.

14. A test device as claimed in claim 1, wherein the transport member is operationally connected to a return spring which urges the transport member to adopt a specified rotational position at which the sealing means can provide a moisture proof seal between the stack of sensors and the transport member.

15. A test device as claimed in claim 1, wherein a portion of the sensor to which a fluid sample is to be applied is not supported by the transport member when in the engagement location.

16. A test device as claimed in claim 1, wherein the transport member has an external profile which is substantially circular in cross section.

17. A test device for testing of analyte concentration in a fluid to be applied thereto, comprising: a housing containing a stack of test strips and having an opening therein; a transport member rotatably mounted in the opening of the housing, having an axis of rotation which spans the opening; the transport member having a recessed region adapted to receive a single test strip; a meter; and spring means which urge the stack towards the transport member; wherein rotation of the transport member with a test strip in the recessed region thereof will bring the said test strip to an engagement location at which the test strip engaged with electrical contacts of the meter and at which the test strip will be accessible to permit a user to apply a drop of fluid thereto.

18. A test device as claimed in claim 17, further including sealing means which make a moisture-proof seal between the transport member and the stack when the transport member is in a specified rotational position.

19. A test device as claimed in claim 1, wherein each sensor in the or each stack comprises a base member having a working area to which the fluid is to be applied, containing the reagent means, and a non-working area adjacent to the working area, wherein the total thickness of the sensor in at least a portion of the non-working area is at least as great as the total thickness of the sensor in the working area.

20. A test device as claimed in claim 19, wherein the total thickness of the sensor in at least a part of the non-working area is greater than the total thickness of the sensor in the working area.

21. A test device for testing of analyte concentration in a fluid to be applied thereto, the device comprising:
  a) a plurality of sensors arranged in a stack, each of said sensors carrying reagent means for producing an electrical signal in response to the concentration of analyte in an applied fluid, each of said sensors having a plurality of electrode tracks for transmitting said electrical signal;
  b) a housing having an opening therein and containing the said stack of sensors;
  c) electrical contacts mounted in relation to the housing for engaging with electrode tracks on a sensor at an engagement location;
  d) a meter connected to the said electrical contacts, having electronics means for producing a signal output which is dependent on the electrical signal from a sensor when the sensor is engaged with the said contacts;
  e) a transport member rotatably mounted in the opening of the housing, having an outer surface which is provided with a recessed region adapted to receive a single sensor from the stack;
  f) spring means within the housing which urge the stack of sensors towards the transport member in a direction substantially perpendicular to a plane containing the axis of rotation of the transport member, and which urge a single sensor into the said recess when the recess is suitably aligned adjacent to the stack;

g) sealing means for making a moisture tight seal between the transport member and the stack when the transport member is in a specified rotational position; and h) wherein rotation of the transport member with a sensor in the recessed region will transport the sensor to the engagement location or to a position where the sensor can be moved to the engagement location, whereby electrode tracks of the sensor can engage with the said electrical contacts.

22. A test device as claimed in claim 1, further including load means for applying a compressive load to a sensor during at least a part of the time when the said sensor is located in the recessed region of the transport member.

23. A test device as claimed in claim 1, further including non-return means which prevent or inhibit transport of a sensor from the engagement location to the magazine and which prevent or inhibit reintroduction of an ejected used sensor to the engagement location.

24. A test device as claimed in claim 23, wherein the said non-return means and the said load means comprise a single resilient and flexible component.

25. A test device as claimed in claim 1, further including ratchet means associated with the stack of sensors which prevent or inhibit movement of the stack in a direction opposite to that in which the spring means urges the stack.

26. A test device for testing of analyte concentration in a fluid to be applied thereto, comprising: a housing containing a stack of test strips and having an opening therein; a transport member rotatably mounted in the opening of the housing; the transport member having a recessed region adapted to receive a single test strip; a meter; and spring means which urge the stack towards the transport member; wherein rotation of the transport member with a test strip in the recessed region thereof will bring the said test strip to an engagement location at which the test strip is engaged with electrical contacts of the meter and at which the test strip will be accessible to permit a user to apply a drop of fluid thereto or to a position from which the sensor can be moved to the engagement location; wherein load means are provided between the transport member and a housing thereof, for applying a compressive load to a sensor during at least a part of the time when the said sensor is located in the recessed region of the transport member.

27. A test device as claimed in claim 1, suitable for use in testing glucose concentration in blood.

\* \* \* \* \*